(12) United States Patent
De Forest et al.

(10) Patent No.: US 8,691,513 B2
(45) Date of Patent: Apr. 8, 2014

(54) METHODS OF USE FOR AN IMMUNOASSAY DETECTING FRAGMENT BA

(75) Inventors: Nikol Lee De Forest, Scotts Valley, CA (US); John Tamerius, San Diego, CA (US); Noah Nasser, San Marcos, CA (US); Patrick Sexton, Windsor, CO (US)

(73) Assignee: Quidel Corporation, San Diego, CA (US)

( * ) Notice: Subject to any disclaimer, the term of this patent is extended or adjusted under 35 U.S.C. 154(b) by 0 days.

(21) Appl. No.: 13/531,269

(22) Filed: Jun. 22, 2012

(65) Prior Publication Data

US 2013/0004973 A1    Jan. 3, 2013

Related U.S. Application Data

(60) Provisional application No. 61/500,574, filed on Jun. 23, 2011.

(51) Int. Cl.
*G01N 33/53*    (2006.01)

(52) U.S. Cl.
USPC ............................................. 435/7.1; 435/7.2

(58) Field of Classification Search
None
See application file for complete search history.

(56) References Cited

U.S. PATENT DOCUMENTS

| | | | |
|---|---|---|---|
| 5,221,616 | A | 6/1993 | Kolb et al. |
| 5,415,994 | A | 5/1995 | Imrich et al. |
| 6,087,120 | A | 7/2000 | Van Oeveren et al. |
| 2005/0260198 | A1 | 11/2005 | Holers et al. |
| 2006/0292141 | A1 | 12/2006 | Holers et al. |
| 2007/0123466 | A1 | 5/2007 | Salmon et al. |
| 2008/0075720 | A1 | 3/2008 | Holers et al. |
| 2008/0102040 | A1 | 5/2008 | Holers et al. |
| 2009/0280124 | A1 | 11/2009 | Labat et al. |

FOREIGN PATENT DOCUMENTS

WO    WO 2009/029669 A1    3/2009

OTHER PUBLICATIONS

Altman and Bland, "Diagnostic test 2: predictive values", BMJ, vol. 309, No. 6947, pp. 102 (1994).
Campbell and Porter, "Molecular cloning and characterization of the gene coding for human complement protein factor B", PNAS, vol. 80, No. 14, pp. 4464-4468 (1983).
Christie and Gagnon, "Amino acid sequence of the Bb fragment from complement Factor B. Sequence of the major cyanogen bromide-cleavage peptide (CB-II) and completion of the sequence of Bb fragment", Biochem. J., vol. 209, No. 1, pp. 61-70 (1983).
Kolb et al., "Ba Bb fragments of factor B activation: fragment production, biological activities, neopitope expression and quantitation in clinical samples", Complement. Inflamm., vol. 6, No. 3, pp. 175-204 (1989).
Lynch et al., "Alternative complement pathway activation fragment Bb in early pregnancy as a predictor of preeclampsia", Am. J. Obstet. Gynecol., vol. 198, No. 4, pp. 385.e1-385.e9 (2008).
Lynch et al., "The interrelationship of complement-activation fragments and angiogenesis-related factors in early pregnancy and their association with pre-eclampsia", B.J.O.G., vol. 117, No. 4, pp. 456-462 (2010).
Nassar et al., "Diagnostic accuracy of clinical examination for detection of non-cephalic presentation in late pregnancy, cross sectional analytic study", BMJ, vol. 333, No. 7568, pp. 578-580 (2006).
Oppermann et al., "Elevated plasma levels of the immunosuppressive complement fragment Ba in renal failure", Kidney Int'l., vol. 40, pp. 939-947 (1991).
Opperman and Götze, "Characterization of physiologic breakdown products of the complement fragment Ba", Mol. Immunol., vol. 31, No. 4, pp. 307-314 (1994).
Raum et al., "Mapping of the structural gene for the second component of complement with respect to the human major histocompatibility complex", Am. J. Hum. Genet., vol. 31, No. 1, pp. 35-41 (1979).
Wan et al., "A longitudinal study of C3, C3d and factor Ba in burn patients in Hong Kong Chinese", Burns, vol. 24, No. 3, pp. 241-244 (1998).

*Primary Examiner* — Jacob Cheu
(74) *Attorney, Agent, or Firm* — Judy M. Mohr; McDermott Will & Emery LLP

(57) ABSTRACT

Methods, compositions and kits for detecting the complement Factor B cleavage product Ba in a biological sample are described. These methods, compositions and kits are useful in convenient, reliable and early diagnosis of or ruling out pre-eclampsia in a pregnant human subject.

8 Claims, 15 Drawing Sheets

SEQ ID NO: 1 - human fragment Ba (residues 26-259 of Factor B):

TPWSLARPQGSCSLEGVEIKGGSFRLLQEGQALEYVCPSGFYPYPVQTRTCRSTGSWSTLKTQDQKTVRK
AECRAIHCPRPHDFENGEYWPRSPYYNVSDEISFHCYDGYTLRGSANRTCQVNGRWSGQTAICDNGAGYC
SNPGIPIGTRKVGSQYRLEDSVTYHCSRGLTLRGSQRRTCQEGGSWSGTEPSCQDSFMYDTPQEVAEAFL
SSLTETIEGVDAEDGHGPGEQQKR

FIG. 1

How positive predictive value, negative predictive value, sensitivity, and specificity are related.

| | | Condition (as determined by "Gold standard") | | |
|---|---|---|---|---|
| | | *Positive* | *Negative* | |
| Test Outcome | *Positive* | True Positive | False Positive (Type I error) | → Positive predictive value $= \dfrac{\Sigma \text{ True Positive}}{\Sigma \text{ Test outcome Positive}}$ |
| | *Negative* | False Negative (Type II error) | True Negative | → Negative predictive value $= \dfrac{\Sigma \text{ True Negative}}{\Sigma \text{ Test outcome Negative}}$ |
| | | → Sensitivity $= \dfrac{\Sigma \text{ True Positive}}{\Sigma \text{ Condition Positive}}$ | → Sensitivity $= \dfrac{\Sigma \text{ True Negative}}{\Sigma \text{ Condition Negative}}$ | |

FIG. 2

| Serum | | | | |
|---|---|---|---|---|
| | Donor 4 | | Donor 8 | |
| Dilution | OD 450nm | Ba (ng/mL) | OD 450nm | Ba (ng/mL) |
| 500 | 1.437 | 1630.10 | 2.240 | 2537.45 |
| 1000 | 0.735 | 1671.10 | 1.122 | 2546.45 |
| 2000 | 0.368 | 1682.30 | 0.544 | 2478.47 |
| 4000 | 0.210 | 1935.15 | 0.302 | 2771.28 |
| 8000 | 0.124 | 2307.83 | 0.159 | 2955.14 |
| 16000 | 0.080 | 3024.23 | 0.090 | 3405.50 |
| 32000 | 0.053 | 4081.80 | 0.057 | 4378.61 |
| 64000 | 0.032 | 5234.12 | 0.038 | 6049.75 |
| | Donor 4 avg: | 2695.83 | Donor 8 avg: | 3512.17 |
| | ± 20%: | 1304-4956 | ± 20%: | 2037-3056 |

| Plasma | | | | |
|---|---|---|---|---|
| | Donor 1 | | Donor 6 | |
| Dilution | OD 450nm | Ba (ng/mL) | OD 450nm | Ba (ng/mL) |
| 500 | 0.627 | 713.24 | 1.082 | 1228.27 |
| 1000 | 0.360 | 822.22 | 0.522 | 1188.15 |
| 2000 | 0.207 | 953.85 | 0.281 | 1286.50 |
| 4000 | 0.134 | 1252.55 | 0.162 | 1498.27 |
| 8000 | 0.094 | 1768.51 | 0.082 | 1557.74 |
| 16000 | 0.068 | 2620.04 | 0.059 | 2292.62 |
| 32000 | 0.046 | 3575.06 | 0.019 | 1650.92 |
| 64000 | 0.036 | 5678.13 | 0.015 | 2674.45 |
| | Donor 1 avg: | 2172.95 | Donor 6 avg: | 1528.92 |
| | ± 20%: | 571-856 | ± 20%: | 983-1474 |

| Urine | | | | |
|---|---|---|---|---|
| | Donor 2 | | Donor 10 | |
| Dilution | OD 450nm | Ba (ng/mL) | OD 450nm | Ba (ng/mL) |
| 4 | 2.078 | 18.84 | 3.801 | 34.43 |
| 8 | 2.691 | 48.77 | 2.891 | 52.40 |
| 16 | 2.762 | 100.12 | 1.345 | 48.82 |
| 32 | 2.447 | 177.41 | 0.584 | 42.60 |
| 64 | 1.389 | 201.62 | 0.289 | 42.36 |
| 128 | 0.846 | 246.19 | 0.148 | 43.92 |
| 256 | 0.375 | 219.48 | 0.052 | 32.24 |
| 512 | 0.216 | 254.13 | 0.043 | 54.45 |
| | Donor 2 avg: | 230.36 | Donor 10 avg: | 44.06 |
| | ± 20%: | 161-242 | ± 20%: | 39-53 |

-Ba ng/mL has been adjusted to account for the dilution factor
-Values shaded are outside the standard range
-Values highlighted in are ± 20% of the first in-range value

FIG. 12

Assay Sensitivity

| expected [ng/mL] Ba | OD (450 nm) | Observed [ng/mL] Ba* | % Recovery |
|---|---|---|---|
| 25 | 3.877 | 14.442 | 57.8 |
| 18 | 3.877 | 14.442 | 80.2 |
| 16.667 | 3.877 | 14.442 | 86.7 |
| 12 | 3.877 | 14.442 | 120.4 |
| 11.111 | 3.877 | 14.442 | 130.0 |
| 10 | 3.657 | 10.523 | 105.2 |
| 8 | 3.511 | 9.001 | 112.5 |
| 7.407 | 3.453 | 8.516 | 115.0 |
| 6.667 | 3.254 | 7.201 | 108.0 |
| 5.333 | 2.668 | 4.869 | 91.3 |
| 4.938 | 2.698 | 4.957 | 100.4 |
| 4.444 | 2.438 | 4.26 | 95.9 |
| 3.556 | 1.921 | 3.185 | 89.6 |
| 3.292 | 1.958 | 3.252 | 98.8 |
| 2.963 | 1.844 | 3.049 | 102.9 |
| 2.37 | 1.246 | 2.105 | 88.8 |
| 2.195 | 1.297 | 2.18 | 99.3 |
| 1.975 | 1.162 | 1.983 | 100.4 |
| 1.58 | 0.867 | 1.562 | 98.9 |
| 1.463 | 0.841 | 1.525 | 104.2 |
| 1.317 | 0.735 | 1.373 | 104.3 |
| 1.053 | 0.612 | 1.192 | 113.2 |
| 0.975 | 0.53 | 1.067 | 109.4 |
| 0.878 | 0.479 | 0.986 | 112.3 |
| 0.702 | 0.424 | 0.759 | 108.1 |
| 0.65 | 0.336 | 0.602 | 92.6 |
| 0.585 | 0.362 | 0.684 | 116.9 |
| 0.468 | 0.281 | 0.504 | 107.7 |
| 0.434 | 0.219 | 0.395 | 91.0 |
| 0.39 | 0.209 | 0.377 | 96.7 |
| 0.312 | 0.166 | 0.3 | 96.2 |
| 0.289 | 0.128 | 0.233 | 80.6 |
| 0.26 | 0.14 | 0.254 | 97.7 |
| 0.208 | 0.136 | 0.247 | 118.8 |
| 0.193 | 0.067 | 0.124 | 64.2 |
| 0.173 | 0.079 | 0.145 | 83.8 |
| 0.139 | 0.097 | 0.178 | 128.1 |
| 0.128 | 0.045 | 0.086 | 67.2 |
| 0.116 | 0.049 | 0.093 | 80.2 |
| 0.092 | 0.068 | 0.127 | 138.0 |
| 0.086 | 0.013 | 0.029 | 33.7 |
| 0.077 | 0.033 | 0.064 | 83.1 |
| 0.062 | 0.038 | 0.072 | 116.1 |
| 0.051 | 0.011 | 0.026 | 51.0 |
| 0.034 | -0.012 | -0.016 | 47.1 |

*Calculated by SoftMax

| Sample: Zero Standard (Std A) | |
|---|---|
| n | 24 |
| mean OD | -0.015 |
| Mean OD | -0.015 |
| SD | 0.013 |
| 3X SD | 0.039 |
| mean OD + 3 SD | 0.024 |
| LOD [ng/mL] | 0.048 |

Key: Entered Data / Phase I Result

Conclusion:

| PDR Requirement (ng/mL) | Phase I Result (ng/mL) | Pass/Fail |
|---|---|---|
| <0.1 | 0.048 | Pass |

FIG. 13

Spike Recovery

| Plasma Sample | Lot Number | Actual Ba ng/ml | Expected Ba ng/ml | % recovery |
|---|---|---|---|---|
| Patient 3 | BRH281277 | 0.223 | ------- | ------- |
| Patient 5 | BRH281279 | 0.496 | ------- | ------- |
| Patient 6 | BRH281280 | 0.268 | ------- | ------- |
| spike control | Ba 3191-40 | 3.015 | *3.000* | *99.5* |
| Patient 3 + Spike | BRH281277 | 3.455 | 3.238 | 107% |
| Patient 5 + Spike | BRH281279 | 3.375 | 3.511 | 96% |
| Patient 6 + Spike | BRH281280 | 3.750 | 3.283 | 114% |

Average Plasma Spike Recovery: 106%

| Serum Sample | Lot Number | Actual Ba ng/ml | Expected Ba ng/ml | % recovery |
|---|---|---|---|---|
| Patient 3 | BRH281267 | 0.349 | ------- | ------- |
| Patient 5 | BRH281269 | 0.496 | ------- | ------- |
| Patient 6 | BRH281270 | 0.268 | ------- | ------- |
| spike control | Ba 3191-40 | 3.015 | *3.000* | *99.5* |
| Patient 3 + Spike | BRH281267 | 3.817 | 3.364 | 113% |
| Patient 5 + Spike | BRH281269 | 3.834 | 3.511 | 109% |
| Patient 6 + Spike | BRH281270 | 3.306 | 3.283 | 101% |

Average Serum Spike Recovery: 108%

| Plasma Sample | Lot Number | Actual Ba ng/ml | Expected Ba ng/ml | % recovery |
|---|---|---|---|---|
| Patient 3 | BRH281287 | 0.225 | ------- | ------- |
| Patient 5 | BRH281289 | 0.188 | ------- | ------- |
| Patient 6 | BRH281290 | 0.195 | ------- | ------- |
| spike control | Ba 3191-40 | 3.015 | *3.000* | *99.5* |
| Patient 3 + Spike | BRH281287 | 1.288 | 3.240 | 40% |
| Patient 5 + Spike | BRH281289 | 0.691 | 3.203 | 22% |
| Patient 6 + Spike | BRH281290 | 0.606 | 3.210 | 19% |

Average Urine Spike Recovery: 27%

FIG. 14

Interfering Substances

| Substance | Physiological Concentration | Assay Concentration | Ba [ng/ml] | Interferrant |
|---|---|---|---|---|
| None | N/A | 0 | 287.59 | N/A |
| Bilirubin | 40 mg/dL | 0.8 mg/dL | 307 | No |
| Cholesterol | 500 mg/dL | 10 mg/dL | 289 | No |
| Glucose | 1200 mg/dL | 24 mg/dL | 307 | No |
| Hemoglobin | 500 mg/dL | 10 mg/dL | 282 | No |
| Albumin | 6000 mg/dL | 120 mg/dL | 278 | No |
| Gamma Gobulin | 6000 mg/dL | 120 mg/dL | 339 | No |
| Triglycerides | 3000 mg/dL | 60 mg/dL | 309 | No |

Range ± 10%: 258-316 ng/ml Ba
Range ± 20%: 230-345 ng/ml Ba

FIG. 15

Cross Reactivity

| Species | OD | Ba (ng/ml) 50 x dilution | Ba ng/ml |
|---|---|---|---|
| Beagle | 0.00 | -0.05 | 0.00 |
| Rabbit | 0.04 | 0.00 | 0.00 |
| Mouse | -0.01 | -0.05 | 0.00 |
| Rhesus Monkey | 2.32 | 2.28 | 114.07 |
| African Green Monkey | 1.05 | 1.01 | 50.41 |
| Cyano Monkey | 1.26 | 1.22 | 60.95 |
| Rat | 0.05 | 0.01 | 0.00 |
| Mouse Plasma | 0.06 | 0.02 | 0.00 |
| Goat | 0.08 | 0.03 | 0.00 |
| Chicken | 0.07 | 0.03 | 0.00 |
| Bovine | 0.50 | 0.45 | 22.68 |
| Guinea Pig | 0.06 | 0.02 | 0.00 |
| Sheep | 0.03 | -0.01 | 0.00 |

| Sample | OD @ 1ug/ml | ng/ml Ba | % Cross Reactivity |
|---|---|---|---|
| Factor B | 2.37 | 2.32 | 0.10 |
| Bb | 0.18 | 0.14 | 0.13 |

FIG. 16

METHODS OF USE FOR AN IMMUNOASSAY DETECTING FRAGMENT BA

CROSS-REFERENCE TO RELATED APPLICATIONS

This application claims priority under 35 U.S.C. §119(e)(1) to U.S. Provisional Patent Application No. 61/500,574, filed 23 Jun. 2011, the contents of which are incorporated herein by reference in their entirety.

REFERENCE TO SEQUENCE LISTING

A "Sequence Listing" is submitted with this application in the form of a text file, created Sep. 7, 2012, and named "556408101 ST25.txt" (12,288 bytes), the contents of which are incorporated herein by reference in their entirety.

TECHNICAL FIELD

The present disclosure generally relates to the field of diagnostics, and, in particular, to a new technique for diagnosis in prenatal medicine, as well as methods and immunoassay kits for diagnosing, predicting or ruling out pre-eclampsia in a pregnant human subject.

BACKGROUND

The complement system is part of an innate system that provides an organism a natural defense against microbial agents and infection without the need for a specific antibody. The complement system consists of a number of small plasma proteins, generally synthesized by the liver, and normally circulating as inactive precursors (pro-proteins). When stimulated by one of several triggers (e.g., microbial polysaccharides or lipids, gram-negative bacterial lipopolysaccharides, and surface determinants present on some viruses, parasites, virally-infected mammalian cells, and cancer cells), proteases in the complement system cleave specific proteins to release cytokines and initiate an amplifying cascade of further cleavages. The end-result of this activation cascade is massive amplification of the response and activation of the cell-killing membrane attack complex (MAC). Over 25 proteins and protein fragments make up the complement system, including serum proteins, serosal proteins, and cell membrane receptors. They account for about 5-15% of the globulin fraction of normal human serum.

Three biochemical pathways comprise the complement system: the classical complement pathway, the alternative complement pathway, and the mannose-binding lectin pathway. Once activated, the three pathways generate homologous variants of the protease C3-convertases, which cleave and activate component C3 to generate C3a and C3b fragments and cause a cascade of further cleavage and activation events. As a major effector molecule of the complement system, C3b binds to the surface of foreign substances, cells and/or pathogens, and opsonizes them for destruction. C3b can originate from classical pathway activation and/or from natural spontaneous hydrolysis of C3 via the alternative pathway.

The alternative pathway is triggered by spontaneous C3 hydrolysis directly due to the breakdown of the thioester bond via condensation reaction (C3 is mildly unstable in aqueous environment) to form C3a and C3b. It does not rely on a pathogen-binding antibodies like the other pathways. The resulting C3b binds to the surface of the activating substance. A central reaction that occurs during alternative complement activation is the conversion of the 93 kDa protein called Complement Factor B (CFB) zymogen to an active proteolytic enzyme. This conversion is accomplished in a two-step reaction. In the first step, Factor B forms a magnesium-dependent complex with C3b or C3(H2O). The C3(H2O)-Factor B complex is formed only in fluid-phase, while the C3b-Factor B complex can be formed either in fluid-phase or on a target surface. In the second step, Factor B is cleaved by Factor D into a 30 to 33 kDa N-terminal fragment "Ba" and a 57 to 60 kDa C-terminal fragment "Bb." The Ba fragment is released, and the Bb fragment that remains in association with C3b comprises the activation pathway fluid-phase C3 convertase, also known as "C3(H2O)Bb" or "C3bBb." Properdin (P) stabilizes the C3bBb complex and protects it from decay; thus, another name for the alternative pathway convertase is "C3bBbP." Although only produced in small amounts, the C3 convertase can cleave multiple native C3 proteins into C3a and C3b. (Christie and Gagnon, 1983, *Biochem. J.* 209(1):61-70). Cleavage of C3 results in the formation of C3bBb3b, the C5 convertase. This enzyme is also stabilized by P to form C3bBb3bP. C5 convertase can cleave many molecules of C5 into C5a and C5b.

Binding of Ba and Bb fragments to B lymphocyte surface receptors modulates the proliferation of pre stimulated B cells.

The C-terminal half of the Bb fragment contains active site residues characteristic of serine proteases, but has a molecular weight twice that of proteinases previously described, suggesting that it is a novel type of serine proteinase. The Bb portion of the factor B gene is about 4 kb long, and the 3-prime end of the gene codes for amino acids 87-505 of Bb and includes the serine protease domain of the protein (Campbell and Porter, *Proc. Natl. Acad. Sci. U.S.A.*, 1983; 80(14):4464-8).

While the complement system serves as a natural defense system against pathogen substances, the consequences of uncontrolled complement activation can be devastating. Continued activation of the cascade attracts leukocytes which release lysosomal enzymes as a byproduct of phagocytosis, and these lysosomal enzymes can cause necrosis of normal tissue. Alternative complement pathway activation has been implicated as a manifestation of disease or trauma states, and cleavage of Factor B is unregulated in a variety of disease states. In autoimmune diseases, the alternative pathway may contribute directly to tissue damage.

Factor B hyperconsumption and increased catabolism, concomitant with factor B fragment production, occurs in diseases and disorders including gram-negative sepsis, autoimmune diseases, burns, chronic glomerulonephritis, lupus nephritis, systemic lupus erythematosus (SLE), fetal loss in at-risk pregnancy, age-related macular degeneration, rheumatoid arthritis, sickle-cell anemia and several skin diseases. Measurement of alternative pathway activation in vivo has been attempted utilized a number of different techniques to quantitate factor B fragments in biological fluids. Plasma concentrations of factor B fragments, especially Ba fragment levels, in SLE patients showed a positive correlation with disease activity scores. Quantitation of Ba fragment levels in SLE plasma samples are believed to be an accurate reflection of disease activity and Ba is a sensitive predictor of impending flare in these patients. (Kolb, et al., 1989, *Complement Inflamm.* 6(3):175-204).

Raum et al. (1979) found a rare genetic type of properdin factor B in 22.6% of patients with insulin-dependent diabetes but in only 1.9% of the general population. (*Am. J. Hum. Genet.*, 1979, 31: 35-41).

Highly elevated plasma levels of fragment Ba were found in patients with chronic renal failure (Oppermann, et al., 1991, *Kidney Intl.*, 40:939-947).

As an indication of an acute inflammatory response, an increase in serum levels of C3, C3d and fragment Ba were found in burn patients within one week post-burn. While the assay was very reliable and accurate in monitoring the changes of these indicators in serum, the ELISA assay for C3d and Ba was believed not to be sensitive enough to detect a very low concentration in urine samples from the burn patients, unless a dramatic increase in C3d and Ba were to take place (Wan, et al., 1998, *Burns*, 24: 241-244).

Animal studies have demonstrated that complement activation is associated with inflammation in the placenta and adverse pregnancy outcomes. Events linked to activation of complement in early pregnancy have been associated with the pathogenesis of pre-eclampsia. In a 2008 study by Lynch, et al., a single plasma sample was obtained from over 701 women before 20 weeks' gestation, and the cohort was followed throughout pregnancy for the development of pre-eclampsia. Elevated levels of the complement activation fragment Bb in plasma at 20 weeks was found to be associated with higher risk of pre-eclampsia. Other significant risk factors for pre-eclampsia included nulliparity, a high body mass index, and maternal medical disease (preexisting maternal hypertension, type 1 diabetes and SLE). Significant risk factors among multiparous women included a history of hypertension in a previous pregnancy and a change of paternity. A model for development of pre-eclampsia was provided, in which complement activation leads to inflammatory events in the trophoblastic tissue and a dysregulation of placental angiogenesis, and when antiangiogenic factors are released (e.g. sFlt1), this causes dysfunction in maternal endothelial cells, leading to pre-eclampsia. Release of Bb into the maternal circulation during the time of uteroplacental vascular remodeling (around 10-20 weeks' gestation) may be a marker of inflammatory events and development of the syndrome later in pregnancy (Lynch, et al., 2008; *Am. J. Obstet. Gynecol.* 198(4):385.e1-385.e9).

Plasma levels of complement activation fragments and serum levels of angiogenesis-related factors and their interrelationship to obesity and pre-eclampsia were also studied in women between 10 and 15 weeks of gestation. While inflammation in early pregnancy is a significant risk factor for pre-eclampsia, and increased concentrations of Factor Bb were found in pre-eclamptic women, there were limitations of the study due to the small number of women who developed pre-eclampsia, and the conclusion from this study was that complement Bb was not a clinically useful marker for pre-eclampsia (Lynch, et al., *B.J.O.G.* 2010, 117:456-462).

Pre-eclampsia is a complex multisystem disease that may occur in as many as 10% of pregnancies and poses a potentially significant health risk to the mother and fetus. Pre-eclampsia can lead to spontaneous pre-term birth (SPTB) and mortality. The cause of pre-eclampsia is unclear, and its clinical manifestations can include an aggregate of symptoms, but pre-eclampsia is classically defined as (1) de novo hypertension with proteinuria at 20 weeks of pregnancy or (2) in the absence of proteinuria, gestational hypertension with cerebral symptoms, epigastric or right upper quadrant pain with nausea or vomiting, thrombocytopenia and abnormal liver function tests. However, extensive evidence suggests that this syndrome starts in early pregnancy, and that the immune system plays an important role in the etiology of pre-eclampsia.

While the simultaneous occurrence of high blood pressure and proteinuria after the twentieth week of pregnancy remain the best indicator of pre-eclampsia, some women often do not present these or other symptoms or feelings of illness until the condition becomes severe. Other symptoms include swelling, sudden weight gain, nausea, vomiting, abdominal, shoulder, and lower back pain, headaches, and vision changes. All of these symptoms however are often associated with normal pregnancy, thereby complicating timely diagnosis of pre-eclampsia. Because causes are unknown and indicators before 20 weeks gestation are lacking, once diagnosed, the only treatment for pre-eclampsia is hospitalization for blood pressure monitoring and regular urine sampling, and the only means of completely alleviating pre-eclampsia is Caesarean section or induction of labor (and therefore delivery of the placenta), often pre-term.

Thus, there is a need for convenient, reliable, early detection of or ruling out pre-eclampsia to prevent unnecessary hospitalization of pregnant women who may have high blood pressure and/or proteinuria, but are not likely to develop pre-eclampsia.

Assessment of Factor B cleavage products in urine, plasma or serum can indicate the extent of alternative pathway activation occurring at the time of sample collection. In particular, cleavage product Ba can serve as an indicator of alternative complement pathway activation in pre-eclampsia. A highly specific antibody, having a high negative predictive value, would mean that a negative result (with no fragment Ba detected in a pregnant woman who may or may not be symptomatic or at risk of pre-eclampsia) was very reliable. Such an assay employing a specific antibody to measure the presence or absence of the Ba fragment in urine, less invasive than measurement of complement activation fragment levels in blood, plasma or serum, would provide a valuable means of ruling out pre-eclampsia at an early stage of pregnancy.

BRIEF SUMMARY

The present disclosure provides methods and compositions for quantitating the concentrations of the Factor B cleavage product Ba in urine, plasma or serum as a diagnostic indicator of or means of ruling out pre-eclampsia and spontaneous pre-term birth in a pregnant subject.

The following aspects and embodiments thereof described and illustrated below are meant to be exemplary and illustrative, not limiting in scope.

BRIEF DESCRIPTION OF THE FIGURES

FIG. 1 shows the amino acid sequence of human complement Factor B fragment Ba (residues 26-259 of Factor B), herein identified as SEQ ID NO: 1.

FIG. 2 illustrates how positive predictive value, negative predictive value, sensitivity and specificity are related.

FIG. 12 presents a dilution series of Ba assays of serum, plasma and urine.

FIG. 13 presents the results of tests for assay sensitivity.

FIG. 14 presents the results of tests for spike recovery in serum, plasma and urine.

FIG. 15 presents the results of tests for interfering substances.

FIG. 16 presents the results of tests for cross reactivity

These and other embodiments are further described in the detailed description that follows.

DETAILED DESCRIPTION

I. Definitions

Before the present methods and compositions are described, it is to be understood that this disclosure is not limited to particular embodiments described, as such may, of course, vary. Several embodiments of the present disclosure are described in detail hereinafter. These embodiments may take many different forms and should not be construed as limited to those embodiments explicitly set forth herein. Rather, these embodiments are provided so that this disclosure will be thorough and complete, and will fully convey the scope of the present disclosure to those skilled in the art. It is also to be understood that the terminology used herein is for the purpose of describing particular embodiments only, and is not intended to be limiting, since the scope of the invention will be limited only by the appended claims.

All patents, applications, published applications and other publications referred to herein are incorporated by reference in their entirety.

As used herein, the following terms are intended to have the following meanings:

As used herein, the singular forms “a,” “an,” and “the” include plural referents unless the context clearly dictates otherwise. Thus, for example, reference to “a protein” includes a plurality of such proteins and reference to “the formulation” includes reference to one or more formulations and equivalents thereof known to those skilled in the art, and so forth.

Where a range of values is provided, it is understood that each intervening value, to the tenth of the unit of the lower limit unless the context clearly dictates otherwise, between the upper and lower limits of that range is also specifically disclosed. Each smaller range between any stated value or intervening value in a stated range and any other stated or intervening value in that stated range is encompassed by this disclosure. The upper and lower limits of these smaller ranges may independently be included or excluded in the range, and each range where either, neither or both limits are included in the smaller ranges is also encompassed by this disclosure, subject to any specifically excluded limit in the stated range. Where the stated range includes one or both of the limits, ranges excluding either or both of those included limits are also within the scope of this disclosure.

“Protein,” “polypeptide,” “oligopeptide,” and “peptide” are used interchangeably to denote a polymer of at least two amino acids covalently linked by an amide bond, regardless of length or post-translational modification (e.g., glycosylation, phosphorylation, lipidation, myristilation, ubiquitination, etc.). Included within this definition are D- and L-amino acids, and mixtures of D- and L-amino acids.

The term “sequence identity” means nucleic acid or amino acid sequence identity in two or more aligned sequences, aligned using a sequence alignment program.

Exemplary computer programs which can be used to determine identity between two sequences include, but are not limited to, the suite of BLAST programs, e.g., BLASTN, BLASTX, and TBLASTX, BLASTP and TBLASTN, publicly available on the Internet at (ncbi.nlm.gov/BLAST/). See, also, Altschul, S. F. et al., 1990 and Altschul, S. F. et al., 1997.

“Percentage of sequence identity” and “percentage homology” are used interchangeably herein to refer to comparisons among polynucleotides and polypeptides, and are determined by comparing two optimally aligned sequences over a comparison window, wherein the portion of the polynucleotide or polypeptide sequence in the comparison window may comprise additions or deletions (i.e., gaps) as compared to the reference sequence (which does not comprise additions or deletions) for optimal alignment of the two sequences. The percentage may be calculated by determining the number of positions at which the identical nucleic acid base or amino acid residue occurs in both sequences to yield the number of matched positions, dividing the number of matched positions by the total number of positions in the window of comparison and multiplying the result by 100 to yield the percentage of sequence identity. Alternatively, the percentage may be calculated by determining the number of positions at which either the identical nucleic acid base or amino acid residue occurs in both sequences or a nucleic acid base or amino acid residue is aligned with a gap to yield the number of matched positions, dividing the number of matched positions by the total number of positions in the window of comparison and multiplying the result by 100 to yield the percentage of sequence identity. Those of skill in the art appreciate that there are many established algorithms available to align two sequences. Optimal alignment of sequences for comparison can be conducted, e.g., by the local homology algorithm of Smith & Waterman, Adv. Appl. Math. 2:482 (1981), by the homology alignment algorithm of Needleman & Wunsch, J. Mol. Biol. 48:443 (1970), by the search for similarity method of Pearson & Lipman, Proc. Nat'l. Acad. Sci. USA 85:2444 (1988), by computerized implementations of these algorithms (GAP, BESTFIT, FASTA, and TFASTA in the GCG Wisconsin Software Package), or by visual inspection (see generally, Current Protocols in Molecular Biology, F. M. Ausubel et al., eds., Current Protocols, a joint venture between Greene Publishing Associates, Inc. and John Wiley & Sons, Inc., (1995 Supplement) (Ausubel)). Examples of algorithms that are suitable for determining percent sequence identity and sequence similarity are the BLAST and BLAST 2.0 algorithms, which are described in Altschul et al. (1990) J. Mol. Biol. 215: 403-410 and Altschul et al. (1977) Nucleic Acids Res. 3389-3402, respectively. Software for performing BLAST analyses is publicly available through the National Center for Biotechnology Information website. The BLAST algorithm parameters W, T, and X determine the sensitivity and speed of the alignment. The BLASTN program (for nucleotide sequences) uses as defaults a wordlength (W) of 11, an expectation (E) of 10, M=5, N=−4, and a comparison of both strands. For amino acid sequences, the BLASTP program uses as defaults a wordlength (W) of 3, an expectation (E) of 10, and the BLOSUM62 scoring matrix (see Henikoff & Henikoff, *Proc. Natl. Acad. Sci. USA* 89:10915 (1989)).

While all of the above mentioned algorithms and programs are suitable for a determination of sequence alignment and % sequence identity, for purposes of the disclosure herein, determination of % sequence identity will typically be performed using the BESTFIT or GAP programs in the GCG Wisconsin Software package (Accelrys, Madison Wis.), using default parameters provided.

Figure 3:
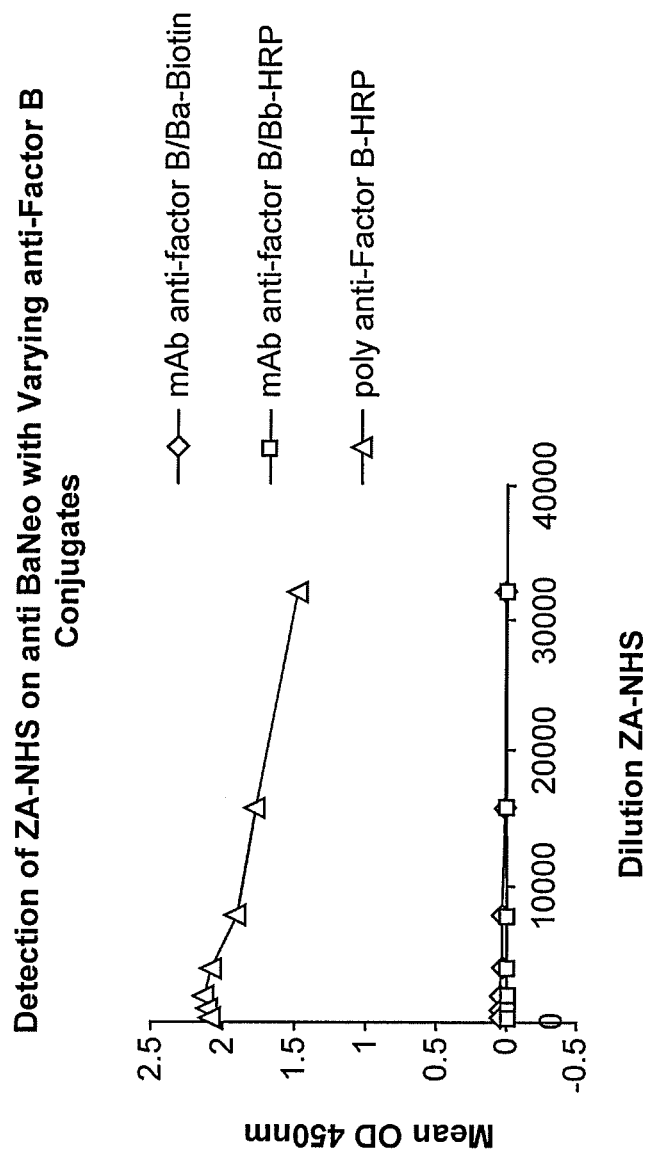
FIG. 3 demonstrates that the mAb anti-human Ba neo and the polyclonal Factor B-HRP conjugated antibody are a highly sensitive matched pair and can detect Ba in a dilution series of zymosan activated normal human serum (ZA-NHS).

The phrase "% sequence identity" refers to the level of nucleic acid or amino acid sequence identity between two or more aligned sequences, when aligned using a sequence alignment program. For example, 70% homology means the same thing as 70% sequence identity determined by a defined algorithm, and accordingly a homologue of a given sequence has greater than 70% sequence identity over a length of the given sequence. Exemplary levels of sequence identity include, but are not limited to 70%, 75% 80%, 85%, 90% or 95% or more sequence identity to a given sequence, e.g., the nucleic acid or amino acid sequence of Factor B, or the Ba fragment, as described herein.

"Associated" refers to coincidence with the development or manifestation of a disease, condition or phenotype. Association may be due to, but is not limited to, genes responsible for housekeeping functions whose alteration can provide the foundation for a variety of diseases and conditions, those that are part of a pathway that is involved in a specific disease, condition or phenotype and those that indirectly contribute to the manifestation of a disease, condition or phenotype.

"Pre-eclampsia" refers to a medical condition affecting a pregnant subject in which one or more of the following symptoms are observed: (1) hypertension (two separate blood pressure readings taken at least 6 hours apart of 140/90 or more) with proteinuria (300 mg of protein in a 24-hour urine sample); (2) gestational hypertension coincident with cerebral symptoms, epigastric or right upper quadrant pain with nausea or vomiting, thrombocytopenia and abnormal liver function tests in the absence of proteinuria. Also of note is a rise in baseline blood pressure (BP) of 30 mmHg systolic or 15 mmHg diastolic, and swelling or edema (especially in the hands and face). Pitting edema (unusual swelling, particularly of the hands, feet, or face, notable by leaving an indentation when pressed on) may also be significant.

The subject's high blood pressure may have been in pre-existence prior to pregnancy, or may be acquired during pregnancy. Hypertension also refers to any relative increase in blood pressure in the pregnant subject, such as an increase in the subject's diastolic pressure of 15 or more or an increase in the systolic pressure of 30 or more relative to the subject's normal values or to values taken at any time point during pregnancy.

As used herein, pre-eclampsia also refers to related disorders such as HELLP syndrome (Hemolysis, Elevated Liver enzymes and Low Platelets) and eclampsia, that are the more severe forms of pre-eclampsia. Eclampsia is associated with seizures and women having this form of pre-eclampsia may not show signs of high blood pressure and proteinuria prior to its onset. "Severe pre-eclampsia" involves a BP over 160/110, and additional symptoms. Pre-eclampsia may progress to eclampsia, characterized by the appearance of tonic-clonic seizures.

Women with higher baseline levels of inflammation stemming from underlying conditions such as chronic hypertension or autoimmune disease may have less tolerance for the inflammatory burden of pregnancy. Pre-eclampsia is more common in women who have preexisting hypertension, diabetes, autoimmune diseases such as lupus, various inherited thrombophilias such as Factor V Leiden, renal disease, obesity, and in women having a family history of pre-eclampsia, and women with a multiple gestation (twins or multiple birth). The single most significant risk for developing pre-eclampsia is having had pre-eclampsia in a previous pregnancy. The pre-eclampsia syndrome may arise from a shallowly implanted placenta which becomes hypoxic, leading to an immune reaction characterized by secretion of upregulated inflammatory mediators from the placenta, and acting on the vascular endothelium. Shallow implantation may stem from the maternal immune system's response to the placenta. However, in many cases of pre-eclampsia, the maternal response to the placenta appears to have allowed for normal implantation.

Pre-eclampsia may be asymptomatic, but one sign often missed or overlooked is epigastric pain, which reflects hepatic involvement and is typical of the HELLP syndrome, may easily be confused with heartburn, a very common problem of pregnancy. It can be distinguished from heartburn when it is not burning in quality, does not spread upwards towards the throat, is associated with hepatic tenderness, may radiate through to the back, and is not relieved by giving antacids. It is often very severe, described by sufferers as the worst pain they have ever experienced. Affected women are not uncommonly referred to general surgeons as suffering from an acute abdomen (for example, acute cholecystitis).

Pre-eclampsia may also occur up to six weeks post-partum.

Other adverse pregnancy outcomes of interest are 1) fetal death after 12 weeks of gestation and not explained by chromosomal abnormalities, anatomic malformations, or congenital infections; 2) neonatal death prior to hospital discharge and not explained by chromosomal abnormalities, anatomic malformations, or congenital infections; 3) preterm delivery prior to 36 weeks and because of gestational hypertension, pre-eclampsia or placental insufficiency; and 4) estimated weight by sonogram and/or birth weight in less than the tenth percentile in the absence of chromosomal or anatomical abnormalities.

The term of pregnancy can be calculated from the date of the last normal menstrual period (LNMP or LMP), or from the date of conception, if known. Childbirth usually occurs about 38 weeks after conception; in women who have a menstrual cycle length of four weeks, this is approximately 40 weeks from the last normal menstrual period (LNMP). The World Health Organization defines normal term for delivery as between 37 weeks and 42 weeks. Pregnancy is considered "at term" when gestation attains 37 complete weeks but is less than 42 (between 259 and 294 days since LMP). Events before completion of 37 weeks (259 days) are considered preterm; from week 42 (294 days) events are considered postterm.

An early sign of complement activation in a pregnant subject at risk of developing pre-eclampsia may be appearance of Ba fragment in a biological fluid such as urine (the Ba fragment is small enough to pass through the glomerular basement membrane), blood, plasma or serum.

A body fluid can be sampled for testing at any time during the pregnancy. A body fluid can be sampled at 1 week from LMP, 2 weeks from LMP, 3 weeks from LMP, 4 weeks from LMP, 5 weeks from LMP, 6 weeks from LMP, 7 weeks from LMP, 8 weeks from LMP, 9 weeks from LMP, 10 weeks from LMP, 11 weeks from LMP, 12 weeks from LMP, 13 weeks from LMP, 14 weeks from LMP, 15 weeks from LMP, 16 weeks from LMP, 17 weeks from LMP, 18 weeks from LMP, 19 weeks from LMP, 20 weeks from LMP, 21 weeks from LMP, 22 weeks from LMP, 23 weeks from LMP, 24 weeks from LMP, 25 weeks from LMP, 26 weeks from LMP, 27 weeks from LMP, 28 weeks from LMP, 29 weeks from LMP, 30 weeks from LMP, 31 weeks from LMP, 32 weeks from LMP, 33 weeks from LMP, 34 weeks from LMP, 35 weeks from LMP, 36 weeks from LMP, 37 weeks from LMP, 38 weeks from LMP, 39 weeks from LMP, 40 weeks from LMP, 41 weeks from LMP or 42 weeks from LMP. A week is named for its end, and each week encompasses the seven days preceding. Thus, week 1 (or the first week) encompasses days 0 to 7, and week two (or "the second week") encompasses days 8 through 14, etc.

As pertains to the present disclosure, the pregnancy term may, alternatively, be counted from the date of conception, if that date is known. If the date of conception is used to determine weeks of pregnancy, the body fluid sampling can occur in any week of pregnancy as described above.

A risk of developing pre-eclampsia may be determined by sampling a pregnant subject's body fluid at a stage of pregnancy between 10 and 19 weeks from LMP or at a stage between 10 and 19 weeks from conception. The body fluid can also be sampled at a stage between 8 and 42 weeks, between 10 and 42 weeks, between 10 and 40 weeks, between 8 and 20 weeks, between 9 and 20 weeks, between 9 and 19 weeks or between 8 and 19 weeks.

As pertains to the present disclosure, a biological fluid can be a solid, or semi-solid sample, including feces, biopsy specimens, skin, nails, and hair, or a liquid sample, such as urine, saliva, sputum, mucous, blood, blood components such as plasma or serum, amniotic fluid, semen, vaginal secretions, tears, spinal fluid, washings, and other bodily fluids. Included among the sample are swab specimens from, e.g., the cervix, urethra, nostril, and throat. Any of such samples may be from a living, dead, or dying animal or a plant. Animals include mammals, such as humans.

"Urine" refers to liquid excrement voided through the urethra or collected from a catheter at any time point before, during, or after pregnancy. Collected urine includes First Morning Void (FMV)—single urine collection upon waking—or Second Morning Void (SMV)—urine collected after FMV.

"Ba" refers to the approximately 30 to 33 kDa amino-terminal fragment (herein identified as SEQ ID NO: 1) of the 93 kDa protein complement factor B (CFB) (NCBI Reference Sequence: NP_001701.2; herein identified as SEQ ID NO: 2) in the alternative complement pathway.

As used herein, the term "neo-epitope of Ba" refers to an epitope or protein determinant recognized by a Ba fragment-specific antibody which does not recognize uncleaved Factor B or fragment Bb.

"Antibody" refers to a polypeptide substantially encoded by an immunoglobulin gene or immunoglobulin genes, or fragments thereof. The recognized immunoglobulin genes include the kappa, lambda, alpha, gamma, delta, epsilon, and mu constant regions, as well as myriad immunoglobulin variable region genes. Light chains are classified as either kappa or lambda. Heavy chains are classified as gamma, mu, alpha, delta, or epsilon, which in turn define the immunoglobulin classes, IgG, IgM, IgA, IgD, and IgE, respectively. Typically, an antibody is an immunoglobulin having an area on its surface or in a cavity that specifically binds to and is thereby defined as complementary with a particular spatial and polar organization of another molecule. The antibody can be polyclonal or monoclonal (abbreviated as mAb or moAb). Antibodies may include a complete immunoglobulin or fragments thereof. Fragments thereof may include Fab, Fv and F(ab')2, Fab', and the like. Antibodies may also include chimeric antibodies or fragment thereof made by recombinant methods.

"Antibody" includes whole antibodies, including those of the IgG, IgM and IgA isotypes, and any antigen binding fragment (i.e., "antigen-binding portion") or single chain thereof. An "antibody" refers to a glycoprotein comprising at least two heavy (H) chains and two light (L) chains interconnected by disulfide bonds, or an antigen binding portion thereof. Each heavy chain is comprised of a heavy chain variable region (abbreviated herein as VH) and a heavy chain constant region. The IgG heavy chain constant region is comprised of four domains, CH1, hinge, CH2 and CH3. Each light chain is comprised of a light chain variable region (abbreviated herein as VL) and a light chain constant region. The light chain constant region is comprised of one domain, CL. The VH and VL regions can be further subdivided into regions of hypervariability, termed complementarity determining regions (CDR), interspersed with regions that are more conserved, termed framework regions (FR). Each VH and VL is composed of three CDRs and four FRs, arranged from amino-terminus to carboxy-terminus in the following order: FR1, CDR1, FR2, CDR2, FR3, CDR3, FR4. The variable regions of the heavy and light chains contain a binding domain that interacts with an antigen. The constant regions of the antibodies may mediate the binding of the immunoglobulin to host tissues or factors, including various cells of the immune system (e.g., effector cells) and the first component (C1q) of the classical complement system.

"Isolated antibody," as used herein, is intended to refer to an antibody which is substantially free of other antibodies having different antigenic specificities (e.g., an isolated antibody that specifically binds to the Ba fragment is substantially free of antibodies that specifically bind antigens other than the Ba fragment). An isolated antibody that specifically binds to an epitope, isoform or variant of the Ba fragment may, however, have cross-reactivity to other related antigens, e.g., from other species (e.g., Factor B fragment Ba species homologs). Moreover, an isolated antibody may be substantially free of other cellular material and/or chemicals. In some embodiments, a combination of "isolated" monoclonal antibodies having different specificities are combined in a well-defined composition.

"Specific binding" refers to antibody binding to a predetermined antigen. Typically, the antibody binds with a dissociation constant (KD) of $10^{-7}$ M or less, and binds to the predetermined antigen with a KD that is at least two-fold less than its KD for binding to a non-specific antigen (e.g., BSA, casein) other than the predetermined antigen or a closely-related antigen. The phrases "an antibody recognizing an antigen" and "an antibody specific for an antigen" are used interchangeably herein with the term "an antibody which binds specifically to an antigen".

"Immunological binding," as used herein, generally refers to the non-covalent interactions of the type that occurs between an antibody, or fragment thereof, and the type 1 interferon or receptor for which the antibody is specific. The strength, or affinity, of immunological binding interactions can be expressed in terms of the dissociation constant (Kd) of the interaction, wherein a smaller Kd represents a greater affinity. Immunological binding properties of selected antibodies can be quantified using methods well known in the art. One such method entails measuring the rates of antigen-binding site/antigen complex formation and dissociation, wherein those rates depend on the concentrations of the complex partners, the affinity of the interaction, and on geometric parameters that equally influence the rate in both directions. Thus, both the "on rate constant" (Kon) and the "off rate constant" (Koff) can be determined by calculation of the concentrations and the actual rates of association and dissociation. The ratio of Koff/Kon enables cancellation of all parameters not related to affinity, and is thus equal to the dissociation constant Kd. See, generally, Davies et al., *Annual Rev. Biochem.* 59:439-473 (1990).

"High affinity" for an IgG antibody refers to an antibody having a KD of $10^{-8}$ M or less, more preferably $10^{-9}$ M or less and even more preferably $10^{-10}$ M or less. However, "high affinity" binding can vary for other antibody isotypes. For example, "high affinity" binding for an IgM isotype refers to an antibody having a KD of $10^{-7}$ M or less, more preferably $10^{-8}$ M or less.

Monoclonal antibodies to a compound may be prepared using any technique which provides for the production of antibody molecules by continuous cell lines in culture. These include, but are not limited to, the hybridoma technique originally described by Kohler & Milstein, 1975, Nature 256:495-497 and/or Kaprowski, U.S. Pat. No. 4,376,110; the human B-cell hybridoma technique described by Kosbor et al., 1983, Immunology Today 4:72 and/or Cote et al., 1983, Proc. Natl. Acad. Sci. USA 80:2026-2030; and the EBV-hybridoma technique described by Cole et al., 1985, Monoclonal Antibodies and Cancer Therapy, Alan R. Liss, Inc., pp. 77-96. In addition, techniques developed for the production of "chimeric antibodies" (Morrison et al., 1984, Proc. Natl. Acad. Sci. USA 81:6851-6855; Neuberger et al., 1984, Nature 312:604-608; Takeda et al., 1985, Nature 314:452-454; Boss, U.S. Pat. No. 4,816,397; Cabilly, U.S. Pat. No. 4,816,567) by splicing the genes from a mouse antibody molecule of appropriate antigen specificity together with genes from a human antibody molecule of appropriate biological activity can be used. Or "humanized" antibodies can be prepared (see, e.g., Queen, U.S. Pat. No. 5,585,089). Alternatively, techniques described for the production of single chain antibodies (see, e.g., U.S. Pat. No. 4,946,778) can be adapted to produce compound-specific single chain antibodies.

Antibody fragments which contain deletions of specific binding sites may be generated by known techniques. For example, such fragments include but are not limited to F(ab')2 fragments, which can be produced by pepsin digestion of the antibody molecule and Fab fragments, which can be generated by reducing the disulfide bridges of the F(ab')2 fragments. Alternatively, Fab expression libraries may be constructed (Huse et al., 1989, Science 246:1275-1281) to allow rapid and easy identification of monoclonal Fab fragments with the desired specificity for the peptide of interest.

The antibody or antibody fragment specific for the desired peptide can be attached, for example, to agarose, and the antibody-agarose complex is used in immunochromatography to purify peptides. See, Scopes, 1984, Protein Purification: Principles and Practice, Springer-Verlag New York, Inc., N.Y., Livingstone, 1974, Methods In Enzymology: Immunoaffinity Chromatography of Proteins 34:723-731.

"Detect" and "detection" have their standard meaning, and are intended to encompass detection, measurement and/or characterization of a selected protein or protein activity. For example, enzyme activity may be "detected" in the course of detecting, screening for, or characterizing inhibitors, activators, and modulators of the protein.

The term "reference level" refers to a reference Ba level that can be previously obtained from the pregnant subject, from another pregnant subject, or can refer to a numerical value derived from multiple normal subjects not having pre-eclampsia. Appropriate reference levels can be measured and chosen to match, for example, the age of the fetus, the age of the mother, blood pressure prior to pregnancy, blood pressure during pregnancy, BMI (body mass index) of the mother, weight of the fetus, prior diagnosis of pre-eclampsia or eclampsia or susceptibility to develop pre-eclampsia or eclampsia. In the comparison of measured Ba level to a reference Ba level, an increase in the Ba level is diagnostic of having or being disposed to having pre-eclampsia.

The term "susceptible" or "predisposition" as used herein describes a subject at risk for developing pre-eclampsia and related disorders. These terms can be used to mean that a subject having a particular genotype and/or haplotype has a higher likelihood than one not having such a genotype and/or haplotype for developing a particular disease or disorder. Risk factors for pre-eclampsia include first pregnancy, pregnancy having more than one gestation, prior history of pre-eclampsia, age (under 18 years old or over 40 years old), high blood pressure prior to pregnancy, diabetes, obesity, polycystic ovarian syndrome, and in vitro fertilization.

"Ameliorate" refers to any indicia of success in the treatment of a pathology or condition, including any objective or subjective parameter such as abatement, remission or diminishing of symptoms or an improvement in a patient's physical or mental well-being. Amelioration of symptoms can be based on objective or subjective parameters; including the results of a physical examination and/or a psychiatric evaluation.

"Label" refers to any moiety that, when attached to a moiety described herein, e.g., a peptide, protein or antibody, renders such a moiety detectable using known detection methods, e.g., spectroscopic, photochemical, electrochemiluminescent, and electrophoretic methods. Various labels suitable for use in the present disclosure include labels which produce a signal through either chemical or physical means, wherein the signal is detectable by visual or instrumental means. Exemplary labels include, but are not limited to, fluorophores and radioisotopes. Such labels allow direct detection of labeled compounds by a suitable detector, e.g., a fluorometer. Such labels can include enzymes and substrates, chromogens, catalysts, fluorescent compounds, chemiluminescent compounds, and radioactive labels. Typically, a visually detectable label is used, thereby providing for instrumental (e.g. spectrophotometer) readout of the amount of the analyte in the sample. Labels include enzymes such as horseradish peroxidase, β-galactosidase, and alkaline phosphatase. Suitable substrates include 3,3',5,5'-tetramethylbenzidine (TMB) and 1,2 dioxetane. The method of detection will depend upon the labeled used, and will be apparent to those of skill in the art. Examples of suitable direct labels include radiolabels, fluorophores, chromophores, chelating agents, particles, chemiluminescent agents and the like.

For such embodiments, the label may be a direct label, i.e., a label that itself is detectable or produces a detectable signal, or it may be an indirect label, i.e., a label that is detectable or produces a detectable signal in the presence of another compound. "Labeled second antibody" refers to an antibody that is attached to a detectable label. The label allows the antibody to produce a detectable signal that is related to the presence of analyte in the fluid sample.

Radioactive labels: Suitable radiolabels include, by way of example and not limitation, $^3$H, $^{14}$C, $^{32}$P, $^{35}$S, $^{36}$Cl, $^{57}$Co, $^{131}$I and $^{186}$Re.

"Chromophore" refers to a moiety with absorption characteristics, i.e., are capable of excitation upon irradiation by any of a variety of photonic sources. Chromophores can be fluorescing or nonfluorescing, and includes, among others, dyes, fluorophores, luminescent, chemiluminescent, and electrochemiluminescent molecules.

Examples of suitable indirect labels include enzymes capable of reacting with or interacting with a substrate to produce a detectable signal (such as those used in ELISA and EMIT immunoassays), ligands capable of binding a labeled moiety, and the like. Suitable enzymes useful as indirect labels include, by way of example and not limitation, alkaline phosphatase, horseradish peroxidase, lysozyme, glucose-6-phosphate dehydrogenase, lactate dehydrogenase and urease. The use of these enzymes in ELISA and EMIT immunoassays is described in detail in Engvall, 1980, *Methods Enzym.* 70: 419-439 and U.S. Pat. No. 4,857,453.

"Substrate," "Support," "Solid Support," "Solid Carrier," or "Resin" are interchangeable terms and refer to any solid phase material. Substrate also encompasses terms such as "solid phase," "surface," and/or "membrane." A solid support can be composed of organic polymers such as polystyrene, polyethylene, polypropylene, polyfluoroethylene, polyethyleneoxy, and polyacrylamide, as well as co-polymers and grafts thereof. A solid support can also be inorganic, such as glass, silica, controlled pore glass (CPG), reverse phase silica or metal, such as gold or platinum. "Solid support" includes membranes (e.g. nitrocellulose), microtiter plate (e.g. PVC, polypropylene, polystyrene), dipstick, test tube, and glass or plastic beads. The configuration of a substrate can be in the form of beads, spheres, particles, granules, a gel, a membrane or a surface. Surfaces can be planar, substantially planar, or non-planar. Solid supports can be porous or non-porous, and can have swelling or non-swelling characteristics. A solid support can be configured in the form of a well, depression, or other container, vessel, feature, or location. A plurality of supports can be configured on an array at various locations, addressable for robotic delivery of reagents, or by detection methods and/or instruments. Methods for immobilizing biomolecules are well known in the art, and the Ba antibody can be attached covalently or non-covalently. In one embodiment, the solid support is a stretavidin coated plate to which a biotinylated Ba antibody is non-covalently attached.

In statistics and diagnostic testing, sensitivity and specificity are statistical measures of the performance of a binary classification test. Sensitivity (also called "recall rate") measures the proportion of actual positives which are correctly identified as such (e.g. the percentage of sick people who are correctly identified as having the condition). Specificity measures the proportion of negatives which are correctly identified (e.g. the percentage of healthy people who are correctly identified as not having the condition). These two measures are closely related to the concepts of type I and type II errors. A theoretical, optimal prediction aims to achieve 100% sensitivity (i.e. predict all people from the sick group as sick) and 100% specificity (i.e. not predict anyone from the healthy group as sick), however theoretically any predictor will possess a minimum error bound known as the Bayes error rate.

"Specificity" relates to the ability of the diagnostic test to identify negative results.

$$\text{Specificity} = \frac{\text{\# of True Negatives}}{\text{\# of True Negatives} + \text{\# of False Positives}}$$

If a test has high specificity, a positive result from the test means a high probability of the presence of the disease for which the test is testing.

"Sensitivity" relates to the ability of the diagnostic test to identify positive results.

$$\text{Sensitivity} = \frac{\text{\# of True Positives}}{\text{\# of True Positives} + \text{\# of False Negatives}}$$

If a test has high sensitivity, a negative result would suggest the absence of disease. For example, a sensitivity of 100% means that the test recognizes all actual positives—i.e. all sick people are recognized as being ill. Thus, in contrast to a high specificity test, negative results in a high sensitivity test are used to rule out the disease.

For any test, there is usually a trade-off between the measures. For example: in an airport security setting in which one is testing for potential threats to safety, scanners may be set to trigger on low-risk items like belt buckles and keys (low specificity), in order to reduce the risk of missing objects that do pose a threat to the aircraft and those aboard (high sensitivity). This trade-off can be represented graphically using a receiver operating characteristic (ROC) curve.

In some embodiments, a ROC is used to generate a summary statistic. Some common versions are: the intercept of the ROC curve with the line at 90 degrees to the no-discrimination line (also called Youden's J statistic); the area between the ROC curve and the no-discrimination line; the area under the ROC curve, or "AUC" ("Area Under Curve"), or A' (pronounced "a-prime"); d' (pronounced "d-prime"), the distance between the mean of the distribution of activity in the system under noise-alone conditions and its distribution under signal-alone conditions, divided by their standard deviation, under the assumption that both these distributions are normal with the same standard deviation. Under these assumptions, it can be proved that the shape of the ROC depends only on d'.

The "positive predictive value (PPV)," or "precision rate" of a test is a summary statistic used to describe the proportion of subjects with positive test results who are correctly diagnosed. It is a measure of the performance of a diagnostic method, as it reflects the probability that a positive test reflects the underlying condition being tested for. Its value does however depend on the prevalence of the outcome of interest, which may be unknown for a particular target population. The PPV can be derived using Bayes' theorem.

The PPV is defined as:

$$PPV = \frac{\text{\# of True Positives}}{\text{\# of True Positives} + \text{\# of False Positives}} = \frac{\text{\# of True Positives}}{\text{\# of Positive calls}}$$

where a "true positive" is the event that the test makes a positive prediction, and the subject has a positive result under the gold standard, and a "false positive" is the event that the test makes a positive prediction, and the subject has a positive result under the gold standard.

"Negative predictive value (NPV)" is defined as the proportion of subjects with a negative test result who are correctly diagnosed. A high NPV means that when the test yields a negative result, it is uncommon that the result should have been positive. In the familiar context of medical testing, a high NPV means that the test only rarely misclassifies a sick person as being healthy. Note that this says nothing about the tendency of the test to mistakenly classify a healthy person as being sick.

The NPV is also defined as:

$$NPV = \frac{\text{\# of True Negatives}}{\text{\# of True Negatives} + \text{\# of False Negatives}} = \frac{\text{\# of True Negatives}}{\text{\# of Negative calls}}$$

where a "true negative" is the event that the test makes a negative prediction, and the subject has a negative result under the gold standard, and a "false negative" is the event that the test makes a negative prediction, and the subject has a positive result under the gold standard.

If the prevalence, sensitivity, and specificity are known, the positive and negative predictive values (PPV and NPV) can be calculated for any prevalence as follows:

$$PPV = \frac{\text{sensitivity} \times \text{prevalence}}{\text{sensitivity} \times \text{prevalence} + (1 - \text{specificity}) \times (1 - \text{prevalence})}$$

$$NPV = \frac{\text{specificity} \times (1 - \text{prevalence})}{(1 - \text{sensitivity}) \times \text{prevalence} + \text{specificity} \times (1 - \text{prevalence})}$$

If the prevalence of the disease is very low, the positive predictive value will not be close to 1 even if both the sensitivity and specificity are high. Thus in screening the general population it is inevitable that many people with positive test results will be false positives.

The rarer the abnormality, the more sure one can be that a negative test indicates no abnormality, and the less sure that a positive result really indicates an abnormality. The prevalence can be interpreted as the probability before the test is carried out that the subject has the disease, known as the prior probability of disease. The positive and negative predictive values are the revised estimates of the same probability for those subjects who are positive and negative on the test, and are known as posterior probabilities. The difference between the prior and posterior probabilities is one way of assessing the usefulness of the test.

For any test result we can compare the probability of getting that result if the patient truly had the condition of interest with the corresponding probability if he or she were healthy. The ratio of these probabilities is called the likelihood ratio, calculated as sensitivity/(1−specificity). (Altman D G, Bland J M (1994). "Diagnostic tests 2: Predictive values". *BMJ* 309 (6947): 102).

"Rule-out criteria" "Rule-Out," or "RO" are terms used in a medical differential diagnosis of a disease or condition, in which certain criteria are evaluated in a clinical decision-making process of elimination or inclusion. A subject is "ruled-out" when, upon consideration of the criteria, the subject has been determined not to have met all or a significant number of criteria for having a disease.

Accordingly, in one aspect of the disclosure, a method is provided for ruling out pre-eclampsia in a pregnant human subject, in which method a sample of a body fluid is obtained from the subject at a time period between 10 and 19 weeks of pregnancy; the sample is contacted with a highly-specific antibody to a neo-epitope on the Ba fragment, which antibody does not recognize Factor B or Bb; the binding of the antibody is assessed to determine whether the antibody detects the presence of Ba in the sample; and, for those pregnant human subjects for which no Ba is detected, pre-eclampsia is ruled out.

In some embodiments, the method of ruling-out involves the generation of a summary statistic and/or an assignment of a risk factor that represents the likelihood of the subject to develop pre-eclampsia at a later date, such as between 20 and 42 weeks of pregnancy or after parturition.

In some embodiments, the body fluid sampled is urine. In some embodiments, the body fluid sampled is blood. In some embodiments, the body fluid sampled is plasma.

In one aspect of the disclosure, a kit is provided for ruling out pre-eclampsia in a pregnant human subject. In some embodiments, the kit comprises a first antibody highly-specific for binding a neo-epitope on Ba and a detection agent. In some embodiments, the kit further comprises a second antibody specific for the first antibody.

In some embodiments, the subject has a hypertensive disorder. In some embodiments, the hypertensive disorder is high blood pressure. In some embodiments, the hypertensive disorder is HELLP syndrome. The high blood pressure may be present in the subject prior to pregnancy or may develop during pregnancy.

In some embodiments, the subject has a pre-existing autoimmune disease, chronic glomerulonephritis, lupus nephritis, systemic lupus erythematosus (SLE), age-related macular degeneration, a rheumatic disease, rheumatoid arthritis, sickle-cell anemia or a skin, joint or connective tissue disease prior to pregnancy. In some embodiments, the subject develops gram-negative sepsis, an autoimmune disease, burn trauma, chronic glomerulonephritis, lupus nephritis, systemic lupus erythematosus (SLE), age-related macular degeneration, a rheumatic disease, rheumatoid arthritis, sickle-cell anemia or a skin, joint or connective tissue disease during pregnancy.

In some embodiments, a reference Ba level is determined from urine sample taken from the subject at an earlier time in pregnancy than the time test is being performed. In some embodiments, the reference urine sample is taken during the first two trimesters of pregnancy. In some embodiments, the urine sample is taken during the first trimester of pregnancy. In some embodiments, the urine sample is taken during the second trimester of pregnancy. In some embodiments, the urine sample is taken during the third trimester of pregnancy.

In some embodiments, the first antibody is a highly specific monoclonal antibody that binds to a neo-epitope on Ba and does not bind to cleavage fragment Bb or to the uncleaved parent Factor B.

In some embodiments, the method has high specificity and low sensitivity for detecting the Ba fragment. In some embodiments, the method has high sensitivity and low specificity for detecting the Ba fragment.

In some embodiments, the level of Ba fragment in a pregnant subject at risk of or having pre-eclampsia can be 0.05 ng/ml higher than the reference, normal or control sample. In some embodiments, the level of Ba fragment in a pregnant subject at risk of or having pre-eclampsia can be 0.07 ng/ml higher than the reference, normal or control sample. In some embodiments, the level of Ba fragment in a pregnant subject at risk of or having pre-eclampsia can be 0.1 ng/ml higher than the reference, normal or control sample. In some embodiments, the level of Ba fragment in a pregnant subject at risk of or having pre-eclampsia can be 0.5 ng/ml higher than the reference, normal or control sample. In some embodiments, the level of Ba fragment in a pregnant subject at risk of or having pre-eclampsia can be 1 ng/ml higher than the reference, normal or control sample. In some embodiments, the level of Ba fragment in a pregnant subject at risk of or having pre-eclampsia can be 2 ng/ml higher than the reference, normal or control sample. In some embodiments, the level of Ba fragment in a pregnant subject at risk of or having pre-eclampsia can be 5 ng/ml higher than the reference, normal or control sample. In some embodiments, the level of Ba fragment in a pregnant subject at risk of or having pre-eclampsia can be 10 ng/ml higher than the reference, normal or control sample.

In some embodiments, the level of Ba fragment in a pregnant subject at risk of or having pre-eclampsia can be 0.05 µg/ml higher than the reference, normal or control sample. In some embodiments, the level of Ba fragment in a pregnant subject at risk of or having pre-eclampsia can be 0.07 µg/ml higher than the reference, normal or control sample. In some embodiments, the level of Ba fragment in a pregnant subject at risk of or having pre-eclampsia can be 0.1 µg/ml higher than the reference, normal or control sample. In some embodiments, the level of Ba fragment in a pregnant subject at risk of or having pre-eclampsia can be 0.5 µg/ml higher than the reference, normal or control sample. In some embodiments, the level of Ba fragment in a pregnant subject at risk of or having pre-eclampsia can be 1 µg/ml higher than the reference, normal or control sample. In some embodiments, the level of Ba fragment in a pregnant subject at risk of or having pre-eclampsia can be 2 µg/ml higher than the reference, normal or control sample. In some embodiments, the level of Ba fragment in a pregnant subject at risk of or having pre-eclampsia can be 5 µg/ml higher than the reference, normal or control sample. In some embodiments, the level of Ba fragment in a pregnant subject at risk of or having pre-eclampsia can be 10 µg/ml higher than the reference, normal or control sample.

In some embodiments, the Ba fragment is detected at 10% of control and is considered diagnostic of having or being susceptible to having pre-eclampsia. In some embodiments, the Ba fragment is detected at 12% of control and is considered diagnostic of having or being susceptible to having pre-eclampsia. In some embodiments, the Ba fragment is detected at 15% of control and is considered diagnostic of having or being susceptible to having pre-eclampsia. In some embodiments, the Ba fragment is detected at 20% of control and is considered diagnostic of having or being susceptible to having pre-eclampsia. In some embodiments, the Ba fragment is detected at 25% of control and is considered diagnostic of having or being susceptible to having pre-eclampsia. In some embodiments, the Ba fragment is detected at 30% of control and is considered diagnostic of having or being susceptible to having pre-eclampsia.

In some embodiments, the level of Ba fragment in a body fluid sample is measured using the proprietary MicroVue® Ba Enzyme Immunoassay (EIA) double immunocapture ELISA kit sold by Quidel (catalog number A033 and A034). The MicroVue® Ba Enzyme Immunoassay Kit measures the amount of complement fragment Ba, an activation fragment of Factor B in human urine, plasma and serum.

In an exemplary use of the MicroVue® kit, the first step involves adding the standards, controls, and test specimens to microassay wells pre-coated with a specific anti-Ba monoclonal antibody. Ba, but not Factor B or other complement activation products present in the Standards, Controls, or specimens will bind to the immobilized anti-Ba monoclonal antibody. After incubation, a wash cycle removes unbound material. In the second step, horseradish peroxidase (HRP) conjugated polyclonal anti-human Factor B antibody is added to each test well. The enzyme conjugated anti-Factor B binds to Ba captured in the microassay wells. After incubation, a wash cycle removes the unbound, excess conjugate. In the third step, a chromogenic enzyme substrate is added to each microassay well. The bound HRP-conjugate reacts with the substrate in the presence of an oxidizing agent, forming a blue color. An exemplary oxidizing agent is hydrogen peroxide. After incubation the enzyme reaction is stopped chemically by addition of an acidic solution, e.g. 1N HCl, that inhibits the HRP conversion of the TMB substrate. The solution color changes to yellow, and the color intensity is measured spectrophotometrically at 450 nm. The color intensity of the reaction mixture is proportional to the concentration of Ba present in the test specimens, Standards, and Controls.

The MicroVue® Ba Enzyme Immunoassay (EIA) kit conforms to the Clinical and Laboratory Standards Institute's (CLSI) standards for precision and accuracy. The kit has a limit of detection (LOD) for Ba of 0.011 ng/mL, a lower limit of quantitation (LLOQ) for Ba of 0.033 ng/mL, and an upper limit of quantitation (ULOQ) of 3.239 ng/mL.

Examples of the antibodies used in the methods and compositions of the present disclosure include monoclonal or polyclonal anti-Factor B, anti-Ba fragment and anti-human Ba neo antibodies.

Illustrative publications describing components of precursor compositions, as well as various antibodies and methods for measuring, or reducing/inhibiting the alternative complement pathway include the following: U.S. Pat. Nos. 5,221,616; 5,415,994; and 6,087,120, U.S. Pat. Pub. Nos. 2005/0260198, 2006/0292141, 2007/0123466, 2008/0102040, 2008/0075720 and 2009/0280124 and PCT Publication WO 2009/029669. All of these patents, applications and publications are incorporated by reference herein, in their entirety.

Kits

Kits for detecting substances present in solid, semi-solid, or liquid biological samples are also provided. The kits may include instructions for obtaining biological samples and contacting them with sample buffer, for mixing the samples with sample buffer, placing labels on the apparatus and recording relevant test data; for shipping the apparatus, and the like. The kits may include instructions for reading and interpreting the results of an assay. The kits may further comprise reference samples that may be used to compare test results with the specimen samples.

EXAMPLES

The following examples describe exemplary assays that can be performed using the presently disclosed methods and compositions. However, the present disclosure shall in no way be considered to be limited to the particular embodiments described below.

Example 1

Basic Assay Protocol 1

100 µL standards and/or samples were added to anti-Ba coated plates, incubated 1 hour at 24° C., and washed five times in 20× wash buffer. 100 µL diluted conjugate was added to wells, and plates were then incubated 30 minutes at 24° C. Wells were washed five times in 20× wash buffer. 100 µL TMB substrate was added to wells and the plates were incubated 15 minutes at 24° C. 100 µL 1N HCl was added to wells to stop the reaction. Optical density was read at 450 nm.

Basic Assay Protocol 2

100 µL standards and/or samples were added to anti-Ba coated plates, incubated 1 hour at 24° C., and washed five times in 20× wash buffer. 100 µL diluted conjugate was added to wells, and plates were then incubated 1 hour at 24° C. Wells were washed five times in 20× wash buffer. 100 µL TMB substrate was added to wells and the plates were incubated 15 minutes at 24° C. 100 µL 1N HCl was added to wells to stop the reaction. Optical density was read at 450 nm.

Example 2

Purification of mAb Anti-Human Ba Neo Antibody

Ascites used to express the monoclonal antibody anti-human Ba (mAb anti-Ba) were produced by Strategic Diagnostics Inc. (SDI). 150 ml of ascites were processed on a 50 ml ProSep®-A affinity column with a yield of 407 mg (2.7 mg of antibody/ml ascites). The final purity was >95% by SDS-PAGE. The final concentration was 1.1 mg/ml and it was stored at −80° C.

Example 3

Proof of Principle and Feasibility for the MicroVue® Ba Assay

Nunc 96 well plates were coated with 10 μg/ml of the anti-Ba neo antibody overnight at 4° C. They were then incubated for one hour with a titration of zymosan activated normal human serum (ZA-NHS). The plate was subsequently washed with wash buffer and then incubated with biotinylated mAb anti Factor B/Ba, and mAb anti-Factor B/Bb-HRP as a control, and goat polyclonal Ab anti-Factor B-HRP. Excess conjugate was then removed, the biotinlyated mAb anti-Factor B/Ba was probed further with a streptavidin-horseradish peroxidase (SA-HRP) conjugate then washed and developed with 3,3',5,5'-Tetramethylbenzidine (TMB) substrate and stopped with 1N HCl. See FIG. 3, showing that the antibody pair of mAb anti-human Ba neo and the polyclonal Factor B-HRP conjugated antibody are a highly sensitive matched pair and can detect Ba in a dilution series of ZA-NHS. The anti-Factor B-HRP is conjugated by Jackson Immunodiagnostics and is also used in the Bb EIA. The anti-human Factor B/Bb-HRP was used as a control to ensure of the neospecficity of the capture antibody.

Example 4

Purification of Complement Fragment Ba

The anti-human Ba neo monoclonal antibody was conjugated to a CNBR-sepharose affinity column for use in purification of the Ba fragment from human serum and human urine. Specifically, the anti-human Ba neo mAb was coupled to 10 ml of 4B sepharose, blocked, washed and equilibrated for use. Zymosan activated normal serum Ba was prepared by incubating 120 ml of normal human serum with 4 mg/ml of zymosan for four hours at 37° C. The zymosan was then spun down and the resultant supernatant was filtered through a 0.2 μm PES filter. 1 L of urine was collected from normal female, sterile filtered and stored at 4° C. for 24 hours prior to purification. The human serum and urine were applied to the affinity column in a high salt matrix (to prevent weak binding proteins from nonspecifically binding), the column was washed with the same high salt matrix and then the protein was eluted from the column using a chaotropic reagent.

Complement fragment Ba was purified from the zymosan activated normal serum and urine by diluting the serum or urine 1:1 with binding buffer (100 mM Tris pH 8.0, 1M NaCl). It was then applied to the affinity column at 1500 cm/hr. The column was subsequently washed with 50 mM Tris pH: 8.0, 500 mM NaCl and the protein was eluted with 50 mM Tris pH: 8.0, 3.5M MgCl2. Fractions with absorbance >10 mAU were then pooled and buffer exchanged into 50 mM Tris pH 7.5, 150 mM NaCl. The pool was concentrated in a 10,000 MWCO ultra filtration device and applied to a 5200 SEC column equilibrated in into 50 mM Tris pH 7.5, 150 mM NaCl. Fractions were collected and all were analyzed for purity by SDS-PAGE. Fractions containing Ba >90% pure were pooled and concentrated further by ultra filtration.

Figure 4:
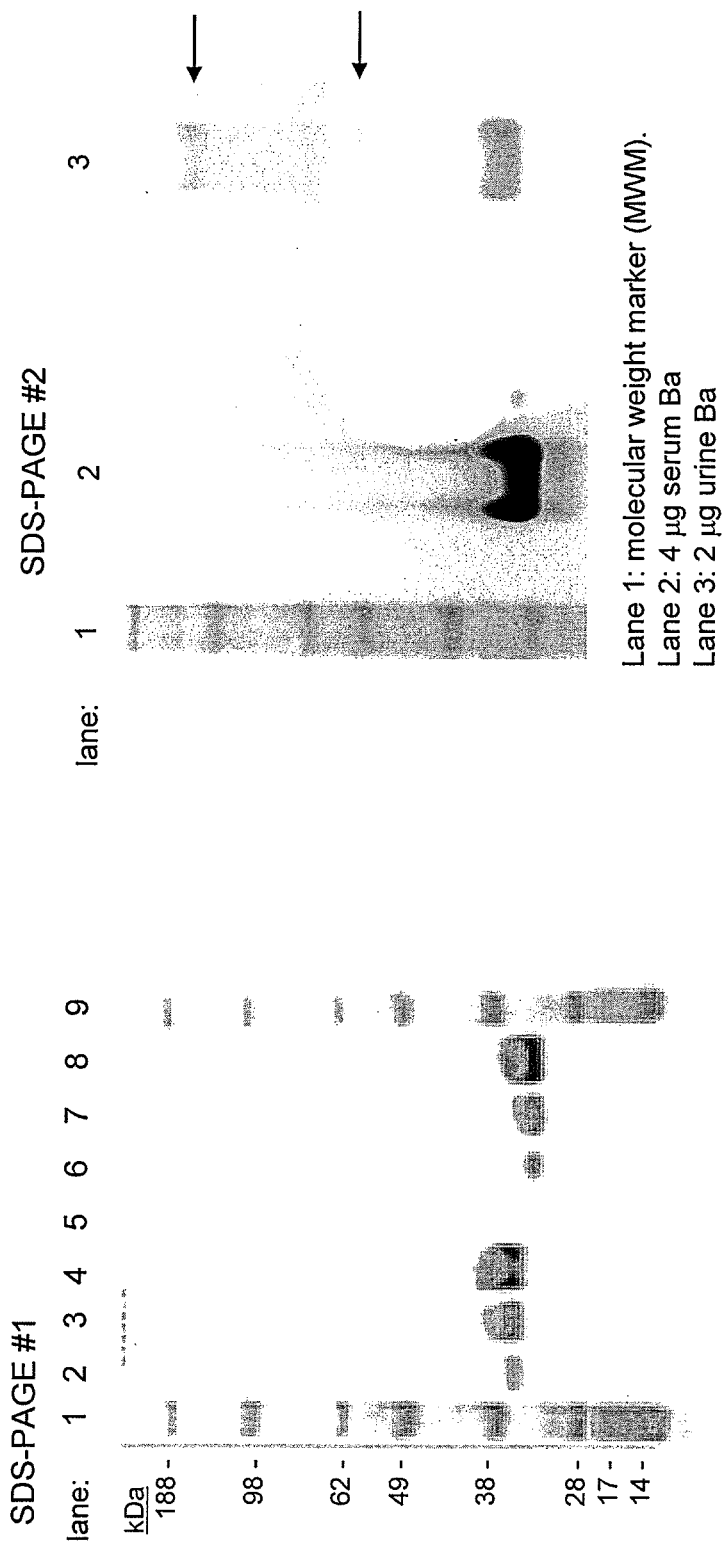
FIG. 4 shows characterization of the neo-specificity of an anti-Ba fragment mAb.

Ba in urine was determined to be glycosylated, resulting migration at a higher molecular weight on the SDS-page gel. In addition, the urine Ba had two high molecular weight bands at ~60 kDa and ~120 kDa. (FIG. 4). Because Ba was purified using an anti-human Ba neo mAb affinity column, it was possible that the anti-human Ba neo mAb cross-reacted with Factor B and/or Bb. To determine whether the high molecular weight bands represented Factor B and/or its cleavage product Bb, or if they were multimers of Ba, the bands were isolated from the SDS-PAGE gel and subjected to tryptic digestion and subsequent LC-MS-MS performed by UC Davis's proteonomics group. Both the Ba purified from urine and the Ba purified from serum were also sent to UC Davis for amino acid analysis, and these amino acid sequences matched the published sequence of Ba. The Ba from serum was used as the "gold standard" in further assays. The ~60 kDa and ~120 kDa bands were confirmed to be multimers of Ba and not Bb or whole Factor B, and no other proteins eluted from the column. Thus it was confirmed that the antibody was specific for the neo epitope of Ba.

Example 5

Initial Dynamic Range

Figure 5:
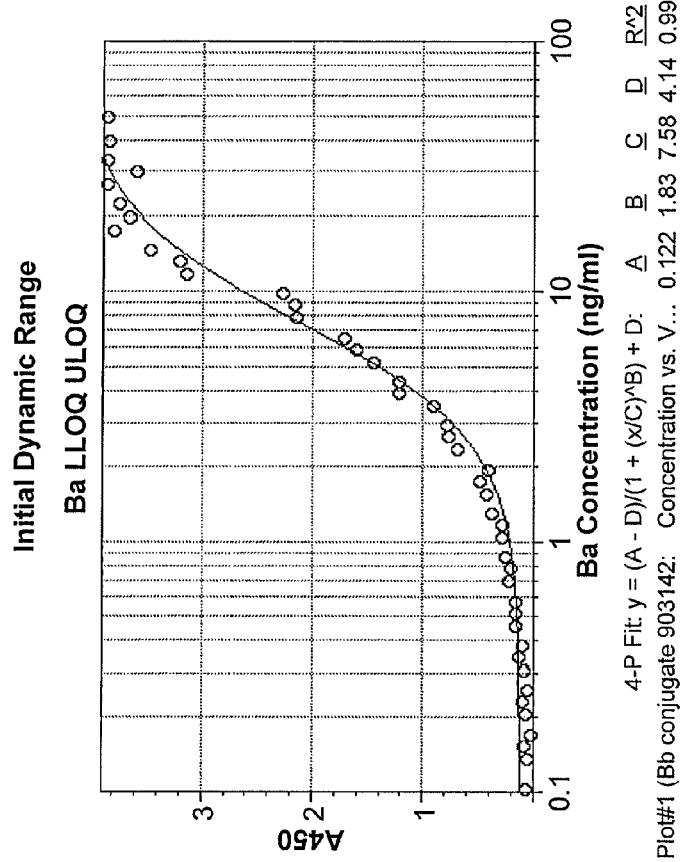
FIG. 5 illustrates an initial dynamic range study of the anti-Ba fragment mAb.

Plates were coated with 100 μL of 10 μg/mL anti-Ba neo antibody in Borate Buffered Saline and incubated at 4° C. overnight, then washed three times in 20× wash buffer. Purified Ba was diluted in SPG Stabilizing Diluent to concentrations from 0.1-50 ng/mL and added to the plate. (FIG. 5). Assay was performed as described in protocol 1 above.

Example 6

Preliminary Linear Range of Assay

Figure 6:
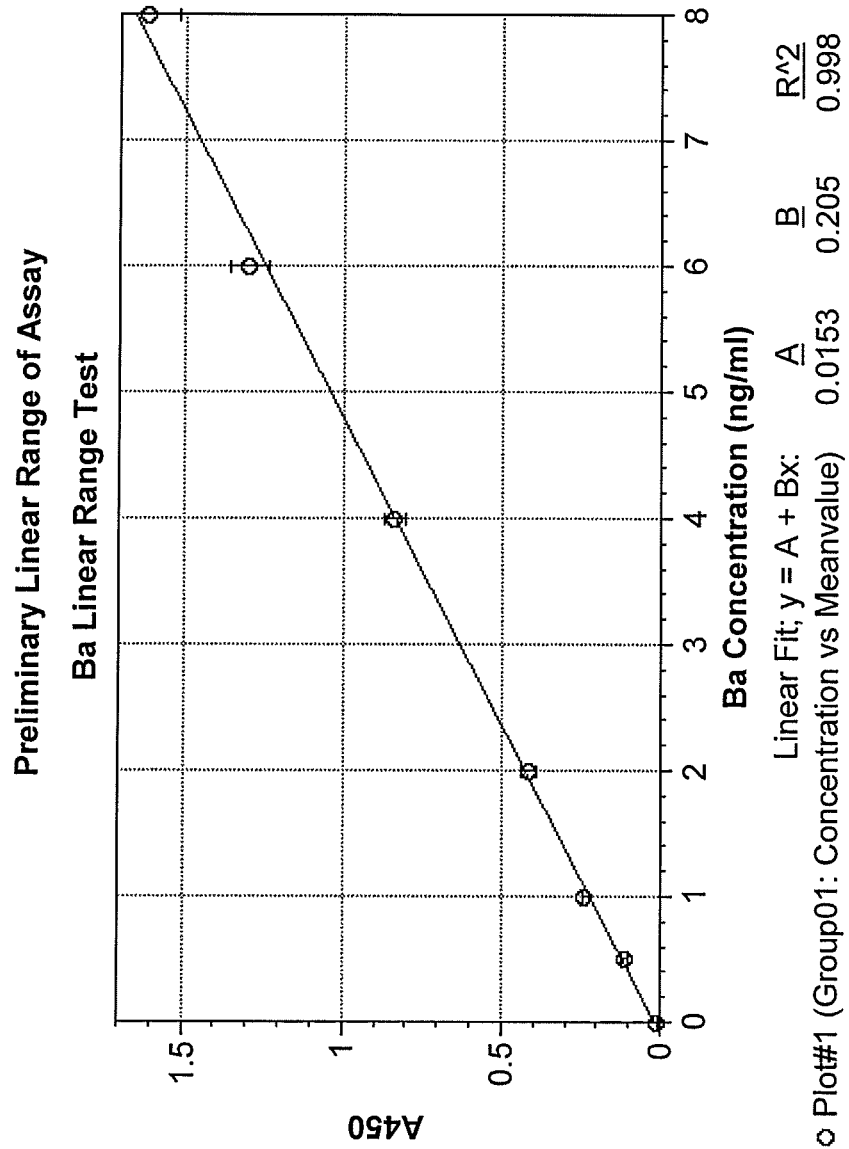
FIG. 6 presents the linearity of the dynamic range of the assay.

Plates were coated with 100 μL of 10 μg/mL anti-Ba neo antibody in Borate Buffered Saline and incubated at 4° C. overnight, then washed 3 times in 20× wash buffer. Purified Ba was diluted in SPG Stabilizing Diluent to 0, 0.5, 1, 2, 4, 6, and 8 ng/mL and added to the plate in triplicate. 100 μL standards and/or samples were added to anti-Ba coated plates and incubated 1 hour at 24° C., then washed five times in 20× wash buffer. 1004 diluted conjugate was added to wells and incubated 30 minutes at 24° C., then plates were washed five times in 20× wash buffer. 100 μL TMB substrate was added to the wells and the plate was incubated 15 minutes at 24° C. 100 μL 1N HCl was added to wells to stop reaction, and optical density read at 450 nm. See FIG. 6, showing that the dynamic range of the preliminary assay is sensitive enough to measure Ba in urine and can be fit using a linear curve fitting algorithm.

Example 7

Conjugate Diluent Testing

Figure 7:
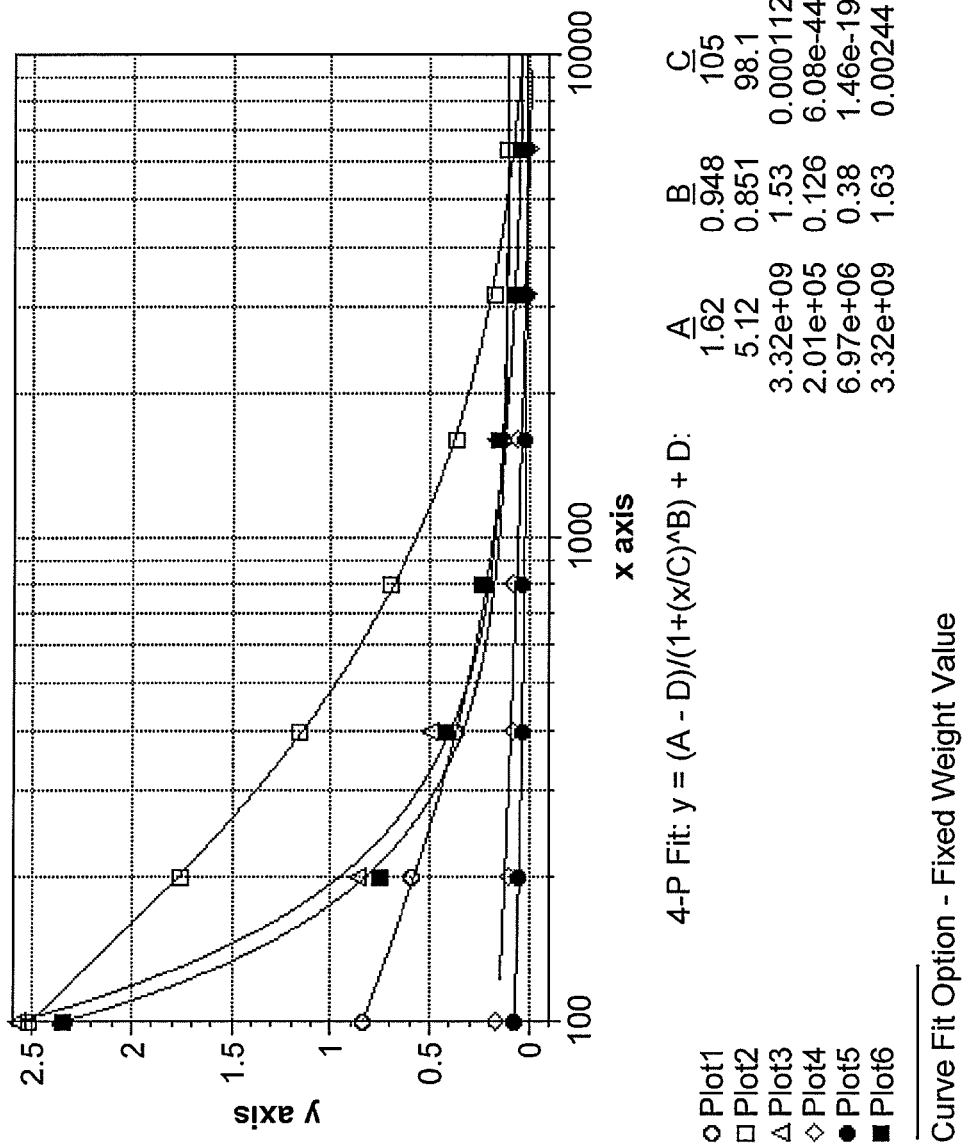
FIG. 7 presents the results of conjugate diluent tests.

A dilution series of freshly made conjugate was made in three different diluents. Plate was coated and washed as above, and each diluent series was tested using 0 ng/mL Ba standard and 6 ng/mL Ba standard, and protocol 2 described above (100 μL diluted conjugate was added to coated wells and incubated 1 hour at 24° C.). See FIG. 7.

Example 8

Plate Coating Titration and Kinetics

Nunc Plates were coated manually with 1, 2, 4, 8, and 10 μg/ml mAb anti-Ba neo in Borate Buffered Saline and incubated overnight at 4° C. The plates were then washed three times with 270 μl 20× wash. The strips were then blocked for three hours with 100 µl of 1% BSA/10% Sucrose. After three hours the block was aspirated and the plates were dried in the environmental chamber at 100° F. and <10% relative humidity for 16 hours. The plates were then pouched and tested.

Testing Conditions: Each plate coating condition was tested using a time flex of the conjugate, with conjugate incubated for 30, 40, 50, 60, 70, and 90 minutes. Four different dilutions of conjugate were tested at these conditions to begin optimizing conjugate dilution as well. Anti-Factor B-HRP was used as conjugate. Ba standards used were 4 ng/mL and 0 ng/mL. Aside from conjugate incubation time, assay was run as described above in Example 7.

Figure 8:
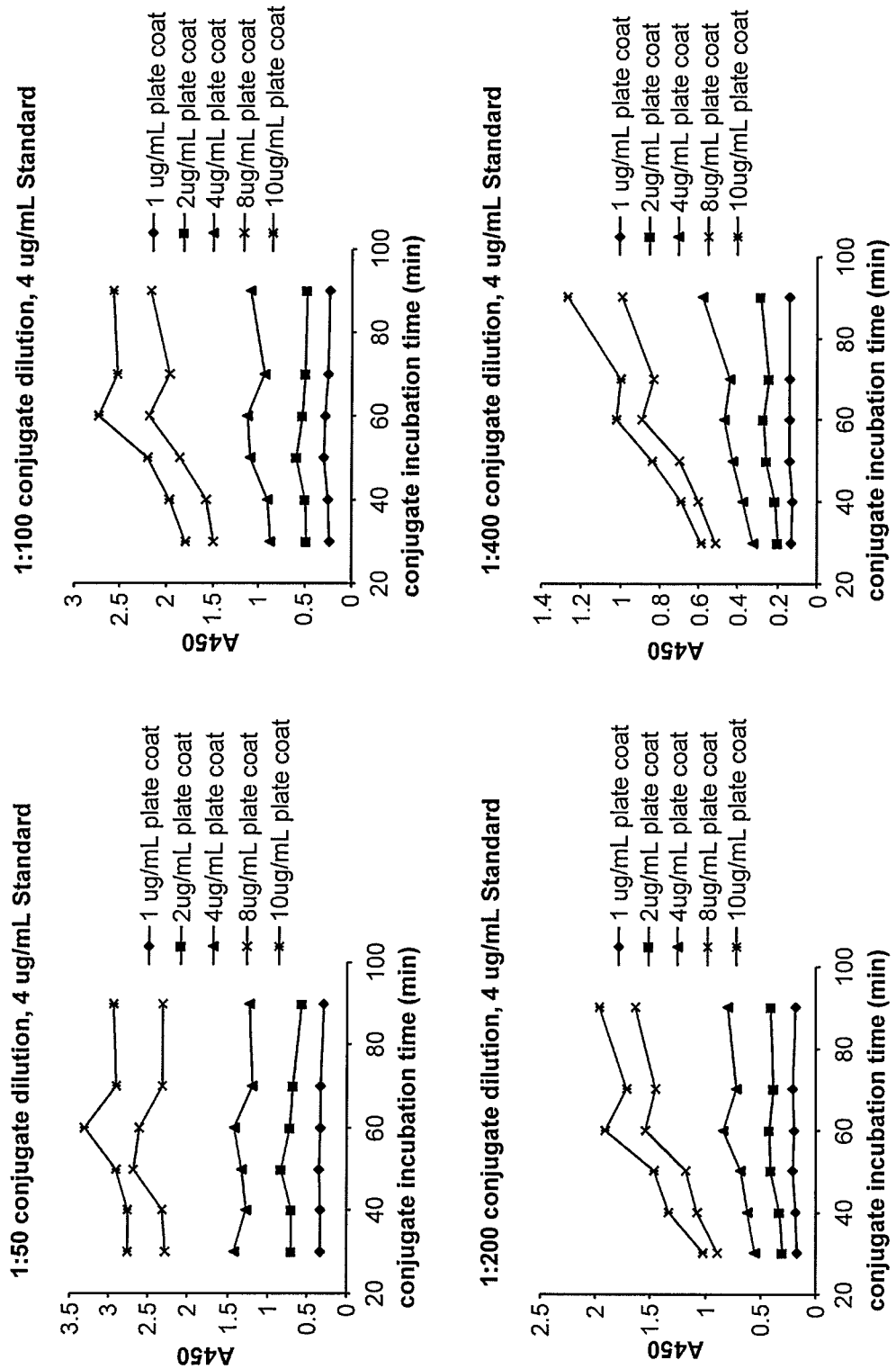
FIG. 8 shows titration and kinetics tests of plate coating.

Results are shown in FIG. 8. The plates coated between 4 µg/mL and 8 µg/mL demonstrated optimal sensitivity, low background, upper OD>1.5 and the binding of Ba complete at all Ba concentrations by 60 minutes. Further optimization was needed between 4 µg/mL and 8 µg/mL of the Ba neo antibody.

Example 9

Plate Coating Concentration Optimization

Nunc Plates were coated manually with 5, 6, and 7 µg/ml MoAb anti-Ba Neo in Borate Buffered Saline. They were incubated overnight at 4° C. The plates were then washed 3×270 µl 20× wash. The strips were then blocked for three hours with 100 µl of 1% BSA/10% Sucrose. After three hours, the block was aspirated and the plates were dried in the environmental chamber at 100° F. and <10% relative humidity for 16 hours. The plates were then pouched and tested.

Testing Conditions: Each plate coating condition was tested as a time flex of the conjugate, with conjugate incubated for 30, 40, 50, 60, 70, and 90 minutes. Four different dilutions of conjugate were tested at these conditions to begin optimizing conjugate dilution as well. Each condition was tested with high (4 µg/mL) and low (0 µg/mL) standard. Aside from conjugate incubation time, assay was run as described above in Example 7.

Figure 9:
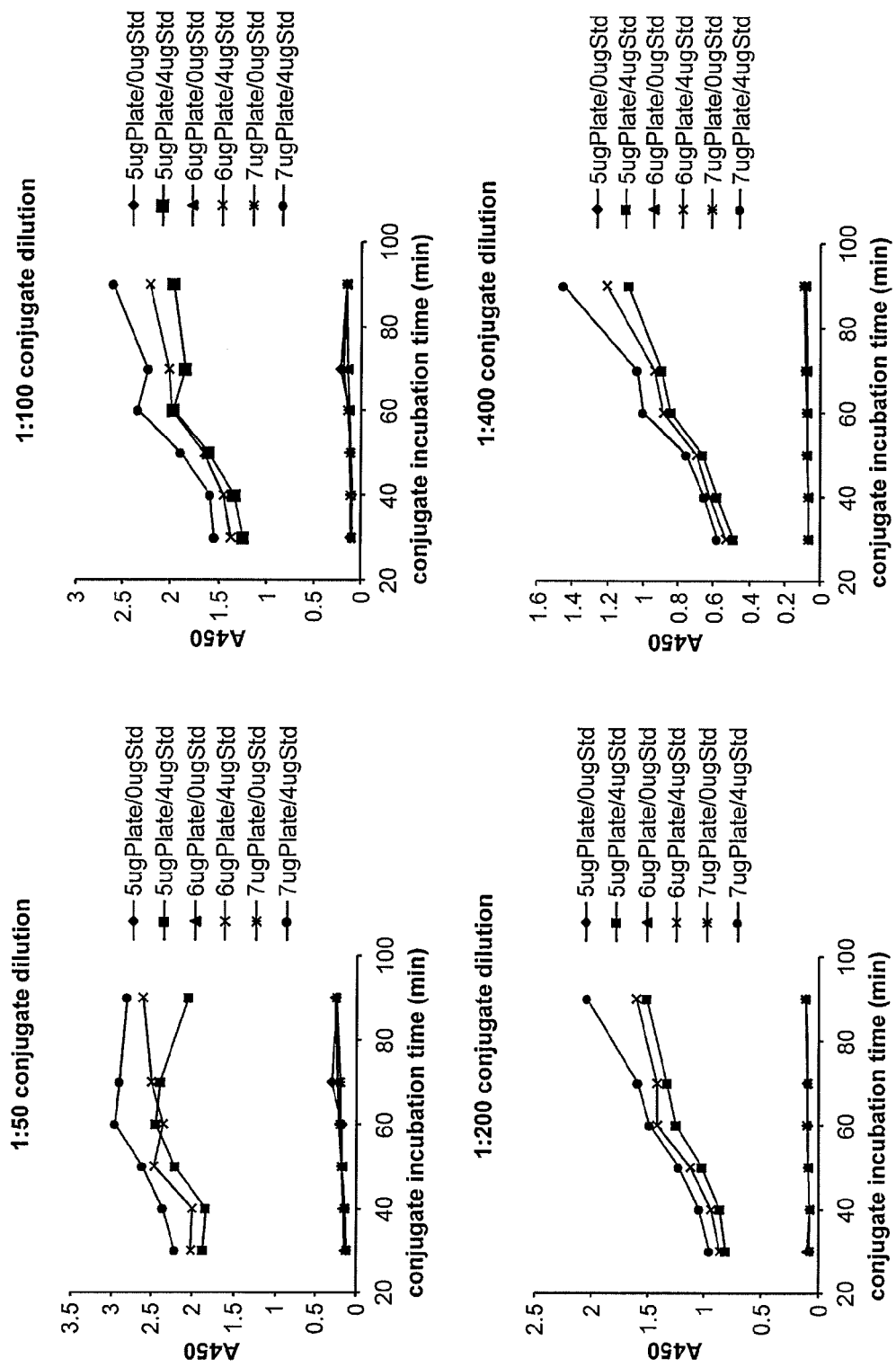
FIG. 9 presents concentration optimization of plate coating.

Results are shown in FIG. 9. Plates coated at 5 µg/mL yielded low background, all concentrations of Ba had reached saturation at 60 minutes incubation time with the samples and had an upper endpoint OD>1.5. The conjugate dilution chosen was 1:75 in combination with the 5 µg/mL coated strips. 50 plates were coated at 5 µg/mL for use in future assays.

Example 10

Western Blots

Figure 10:
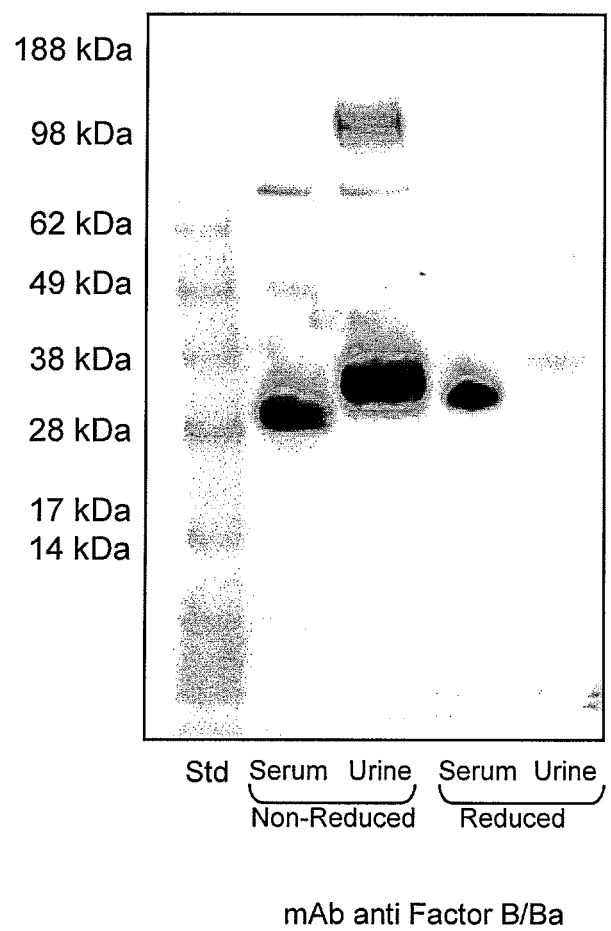
FIG. 10 shows a Western blot using an anti-Ba antibody.

Ba purified from serum and Ba purified from urine were run non-reduced and reduced on a 12-well NuPAGE 4-12% Bis-Tris Gel. The gel was transferred to a membrane using the Invitrogen iBlot® system. The membrane was blocked for one hour in Odyssey® blocking buffer. Primary antibody mAb anti Factor B/Ba was diluted 1/5,000 in blocking buffer with 0.1% Tween-20. The membrane was incubated in diluted primary antibody solution overnight. After incubation, the membrane was washed in TBS+0.1% Tween-20 three times, for a minimum of 15 minutes each wash. Secondary antibody Donkey anti-Mouse IRDye 800CW was diluted 1/10,000 in blocking buffer with 0.1% Tween-20. The washed membrane was incubated in this diluted secondary antibody solution for 45 minutes. After incubation, the membrane was washed three times in TBS+0.1% Tween-20 for a minimum of 15 minutes each wash, and one time for 20 minutes in TBS without Tween. Washed membrane was scanned on Odyssey® scanner. See FIG. 10, showing that the anti-Ba antibody recognized all proteins in the western blot except reduced urine Ba.

Figure 11:
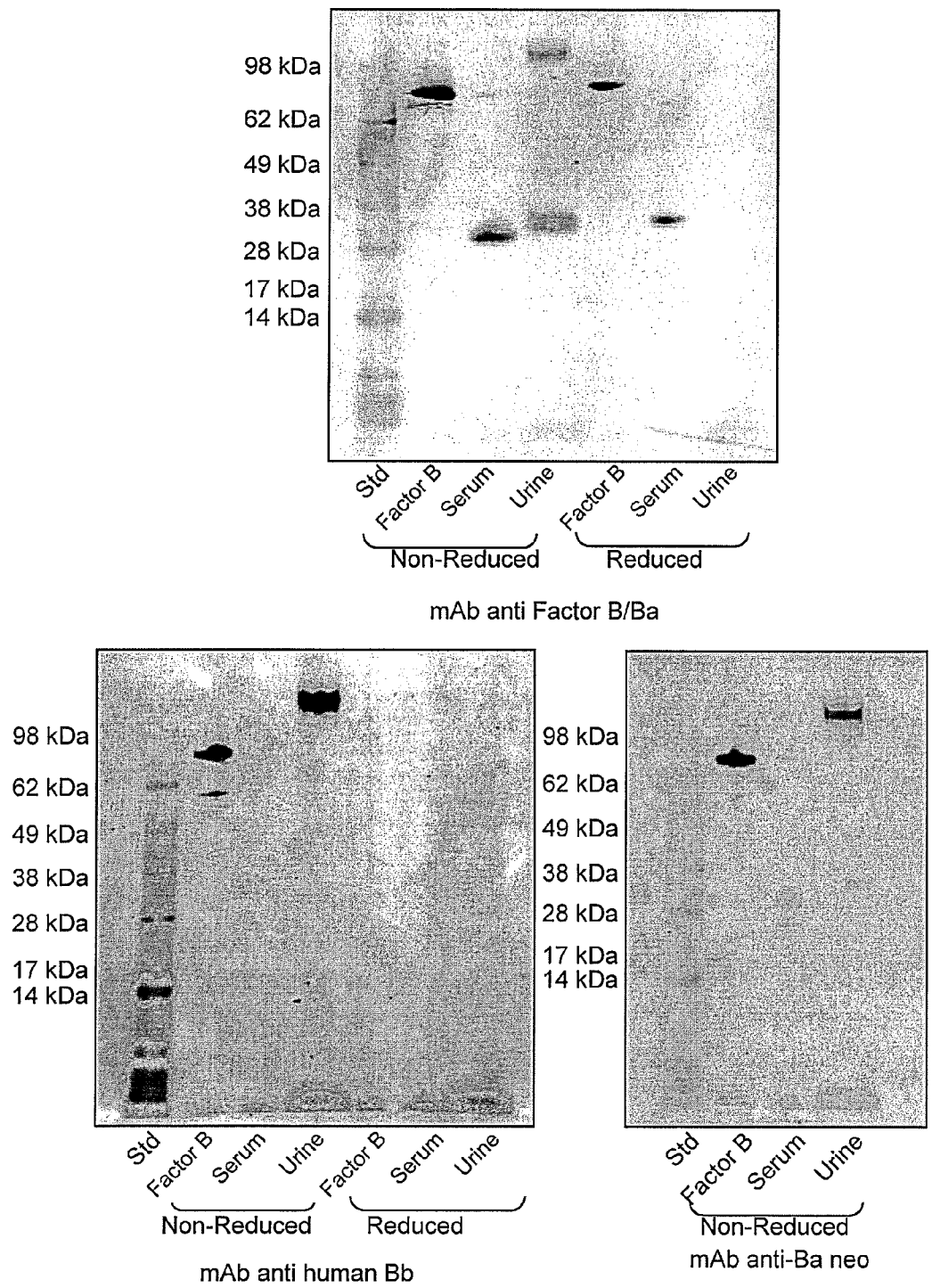
FIG. 11 presents three Western blots using anti-Ba antibodies.

Additionally, in three separate experiments Factor B, Ba purified from serum and Ba purified from urine were run non-reduced and reduced on a 12-well NuPAGE 4-12% Bis-Tris Gel. After transferring the gels to membrane using the iBlot®, the blocking, dilutions, incubations and washes were as described above in Example 6. However, each experiment used a different primary antibody. The three primary antibodies were: mAb anti-human Factor B/Ba, mAb anti-human Bb and mAb anti-Ba neo. See FIG. 11, showing that the higher molecular weight impurities in urine Ba are recognized by all three antibodies. The higher molecular weight impurity was greater in molecular weight than a purified Factor B control on the SDS-Page. It was hypothesized that if Ba forms multimers of four, the impurities would run at the apparent molecular weight seen on the gel. The higher molecular weight multimers were then excised from the SDS-Page gel and subject to tryptic digestion and then identification by LC-MS-MS where they were confirmed to be Ba multimers by UC Davis Proteonomics Core Laboratory.

Example 11

Sample Dilution Series

A dilution series was set up to measure Ba levels in donors' serum, urine, and plasma samples. 20 urine, serum and plasma samples from normal pregnant subjects were measured for presence of Ba using MicroVue® Ba Enzyme Immunoassay (EIA). The data range was 0.07 ng/ml to 1.54 µg/ml (not creatine adjusted). Each dilution series was run in triplicate in the assay, and the values were calculated based on the standard curve and dilution factor. Assay was run on the 5 µg/mL anti-Ba coated plates as described in protocol 2 above. The conjugate used was the new anti-Factor B-HRP conjugate from Jackson, pre-diluted to optimal concentration. Results are shown in FIG. 12. Serum, plasma and urine were found to be linear for >3 two-fold serial dilutions.

Example 12

Assay Sensitivity ULOQ/LOQ/LOD

Purified Ba was diluted in SPG Stabilizing Diluent to concentrations from 0.034-25 ng/mL and added to the 5 µg/mL anti-Ba coated plate. The Jackson conjugate was used. Assay was performed as described above in Example 7. Results are presented in FIGS. 13. LOD was observed to be 0.048 ng/mL. ULOQ was observed to be 10 ng/mL. LLOQ was observed to be 0.208 ng/mL.

Example 13

Spike Recovery—Urine, Serum, Plasma

Urine, Plasma, and Serum samples were diluted in complement specimen diluent and spiked with purified Ba. The spiked samples, non-spiked samples, and a spike control (purified Ba spiked into specimen diluent rather than a sample) were added in triplicate to the 5 µg/mL anti-Ba coated plate. The Jackson conjugate was used. Assay was performed as described above in Example 7. Results are shown in FIG. 14.

Example 14

Interfering Substances

Interfering substances are molecules likely to be found in the sample matrix that may cause a positive or negative bias of the true analyte quantitation. Defined amounts of these potential interferants were added individually to the samples and the bias, if any, was determined. In the present study, a substance that results in a bias of 100+/−10% recovery of the analyte was considered an interferant. As shown in FIG. 15, several potential interferants were evaluated, but no interfering substances were found.

Example 15

Cross Reactivity

Cross reactivity of other species and proteins were evaluated. Serum samples for each species were diluted 50× in specimen diluent and run in the Ba EIA per standard protocol. Cross reactivity (shown in bold text in FIG. 16) was identified in the three species of monkeys tested, thus meeting PDR requirements. The assay is also cross reactive with Bovine Ba. No other species were identified as cross reactive. Cross reactivity of Factor B and Bb was less than <0.15% which is a valid result per the PDR specification and the Bioanalytical Method Validation Document from the CDER.

Example 16

Testing Patients for Elevated Ba Fragment Levels in Biological Samples

Testing for the complement activation product by immunoassay of fragment Ba levels is performed on 1000 patients having or not having high blood pressure (HBP), systemic lupus erythematosus (SLE) and/or antiphospholipid (aPL) antibodies divided into nine groups:

Group 1: (HBP+/aPL+/SLE−, n=100);
Group 2: (HBP−/aPL+/SLE−, n=100);
Group 3: (HBP+/aPL−/SLE−, n=100);
Group 4: (HBP−/aPL−/SLE−, n=100);
Group 5: (HBP+/aPL+/SLE+, n=100);
Group 6: (HBP−/aPL+/SLE+, n=100);
Group 7: (HBP+/aPL−/SLE+, n=100);
Group 8: (HBP−/aPL−/SLE+, n=100);
Group 9 (Healthy Controls): (HBP−/aPL−/SLE−, n=200).

Patients are recruited prior to 12 weeks of gestation and are seen monthly until the end of their pregnancy and also once post-partum. There may be from 2 to 10 longitudinal visits for each patient. On average, there are 6 or 7 longitudinal visits per patient. During each visit, clinical data and biological samples of plasma, serum, DNA, RNA and urine are collected. Ba levels are tested, and additional analytes such as C4d, Bb, C3a, C3b or C5a, may be tested for comparison. Test plates may contain samples from patients with adverse outcomes, without adverse outcomes, and healthy controls.

While various specific embodiments have been illustrated and described, skilled artisans will recognize various modifications, permutations, additions and sub-combinations thereof, and will appreciate that these can be made without departing from the spirit and scope of the present disclosure. Therefore, it is to be understood that the disclosure is not to be limited to the specific embodiments disclosed herein, as such are presented by way of example. Although specific terms are employed herein, they are used in a generic and descriptive sense only and not for purposes of limitation.

All literature and similar materials cited in this application, including, but not limited to, patents, patent applications, articles, books, treatises, internet web pages and other publications cited in the present disclosure, regardless of the format of such literature and similar materials, are expressly incorporated by reference in their entirety for any purpose to the same extent as if each were individually indicated to be incorporated by reference. In the event that one or more of the incorporated literature and similar materials differs from or contradicts the present disclosure, including, but not limited to defined terms, term usage, described techniques, or the like, the present disclosure controls.

What is claimed is:

1. A method for ruling out pre-eclampsia in a pregnant human subject, comprising:
    obtaining, at a time period between 10 and 19 weeks of pregnancy, a sample of a body fluid from the subject;
    contacting the sample with a highly-specific antibody to a neo-epitope on fragment Ba (residues 26-259 of human complement Factor B, herein identified as SEQ ID NO: 1), which antibody does not substaintially recognize Factor B or Bb;
    assessing whether the antibody detects the presence of Ba in the sample; and
    identifying as "ruled-out" those pregnant human subjects for which no Ba is detected.

2. The method of claim 1, wherein a risk factor of developing pre-eclampsia at a later point in pregnancy or after parturition is assigned.

3. The method of claim 1, wherein the body fluid is urine.

4. The method of claim 1, wherein the body fluid is blood.

5. The method of claim 1, wherein the body fluid is plasma.

6. The method of claim 1, wherein the body fluid is serum.

7. A kit for use in the method of claim 1, comprising:
    a first antibody highly-specific for binding a neo-epitope on Ba but does not substantially recognize Factor B or Bb; and
    a detection agent.

8. The kit of claim 7, further comprising a second antibody specific for the first antibody.

* * * * *

```
                        SEQUENCE LISTING

<160> NUMBER OF SEQ ID NOS: 2

<210> SEQ ID NO 1
<211> LENGTH: 234
<212> TYPE: PRT
<213> ORGANISM: Homo sapiens

<400> SEQUENCE: 1

Thr Pro Trp Ser Leu Ala Arg Pro Gln Gly Ser Cys Ser Leu Glu Gly
1               5                   10                  15

Val Glu Ile Lys Gly Gly Ser Phe Arg Leu Leu Gln Glu Gly Gln Ala
            20                  25                  30

Leu Glu Tyr Val Cys Pro Ser Gly Phe Tyr Pro Tyr Pro Val Gln Thr
        35                  40                  45

Arg Thr Cys Arg Ser Thr Gly Ser Trp Ser Thr Leu Lys Thr Gln Asp
    50                  55                  60

Gln Lys Thr Val Arg Lys Ala Glu Cys Arg Ala Ile His Cys Pro Arg
65                  70                  75                  80

Pro His Asp Phe Glu Asn Gly Glu Tyr Trp Pro Arg Ser Pro Tyr Tyr
```

Asn Val Ser Asp Glu Ile Ser Phe His Cys Tyr Asp Gly Tyr Thr Leu
            85                  90                  95
Arg Gly Ser Ala Asn Arg Thr Cys Gln Val Asn Gly Arg Trp Ser Gly
        100                 105                 110
Gln Thr Ala Ile Cys Asp Asn Gly Ala Gly Tyr Cys Ser Asn Pro Gly
        115                 120                 125
Ile Pro Ile Gly Thr Arg Lys Val Gly Ser Gln Tyr Arg Leu Glu Asp
        130                 135                 140
Ser Val Thr Tyr His Cys Ser Arg Gly Leu Thr Leu Arg Gly Ser Gln
145                 150                 155                 160
Arg Arg Thr Cys Gln Glu Gly Gly Ser Trp Ser Gly Thr Glu Pro Ser
                165                 170                 175
Cys Gln Asp Ser Phe Met Tyr Asp Thr Pro Gln Glu Val Ala Glu Ala
            180                 185                 190
Phe Leu Ser Ser Leu Thr Glu Thr Ile Glu Gly Val Asp Ala Glu Asp
        195                 200                 205
Gly His Gly Pro Gly Glu Gln Gln Lys Arg
        210                 215                 220

225                 230

<210> SEQ ID NO 2
<211> LENGTH: 764
<212> TYPE: PRT
<213> ORGANISM: Homo sapiens

<400> SEQUENCE: 2

Met Gly Ser Asn Leu Ser Pro Gln Leu Cys Leu Met Pro Phe Ile Leu
1               5                   10                  15
Gly Leu Leu Ser Gly Gly Val Thr Thr Thr Pro Trp Ser Leu Ala Arg
            20                  25                  30
Pro Gln Gly Ser Cys Ser Leu Glu Gly Val Glu Ile Lys Gly Gly Ser
        35                  40                  45
Phe Arg Leu Leu Gln Glu Gly Gln Ala Leu Glu Tyr Val Cys Pro Ser
    50                  55                  60
Gly Phe Tyr Pro Tyr Pro Val Gln Thr Arg Thr Cys Arg Ser Thr Gly
65              70                  75                  80
Ser Trp Ser Thr Leu Lys Thr Gln Asp Gln Lys Thr Val Arg Lys Ala
            85                  90                  95
Glu Cys Arg Ala Ile His Cys Pro Arg Pro His Asp Phe Glu Asn Gly
        100                 105                 110
Glu Tyr Trp Pro Arg Ser Pro Tyr Tyr Asn Val Ser Asp Glu Ile Ser
        115                 120                 125
Phe His Cys Tyr Asp Gly Tyr Thr Leu Arg Gly Ser Ala Asn Arg Thr
        130                 135                 140
Cys Gln Val Asn Gly Arg Trp Ser Gly Gln Thr Ala Ile Cys Asp Asn
145                 150                 155                 160
Gly Ala Gly Tyr Cys Ser Asn Pro Gly Ile Pro Ile Gly Thr Arg Lys
                165                 170                 175
Val Gly Ser Gln Tyr Arg Leu Glu Asp Ser Val Thr Tyr His Cys Ser
            180                 185                 190
Arg Gly Leu Thr Leu Arg Gly Ser Gln Arg Arg Thr Cys Gln Glu Gly
        195                 200                 205
Gly Ser Trp Ser Gly Thr Glu Pro Ser Cys Gln Asp Ser Phe Met Tyr
        210                 215                 220
Asp Thr Pro Gln Glu Val Ala Glu Ala Phe Leu Ser Ser Leu Thr Glu

```
            225                 230                 235                 240

Thr Ile Glu Gly Val Asp Ala Glu Asp Gly His Gly Pro Gly Glu Gln
                245                 250                 255

Gln Lys Arg Lys Ile Val Leu Asp Pro Ser Gly Ser Met Asn Ile Tyr
                260                 265                 270

Leu Val Leu Asp Gly Ser Asp Ser Ile Gly Ala Ser Asn Phe Thr Gly
                275                 280                 285

Ala Lys Lys Cys Leu Val Asn Leu Ile Glu Lys Val Ala Ser Tyr Gly
                290                 295                 300

Val Lys Pro Arg Tyr Gly Leu Val Thr Tyr Ala Thr Tyr Pro Lys Ile
305                 310                 315                 320

Trp Val Lys Val Ser Glu Ala Asp Ser Ser Asn Ala Asp Trp Val Thr
                325                 330                 335

Lys Gln Leu Asn Glu Ile Asn Tyr Glu Asp His Lys Leu Lys Ser Gly
                340                 345                 350

Thr Asn Thr Lys Lys Ala Leu Gln Ala Val Tyr Ser Met Met Ser Trp
                355                 360                 365

Pro Asp Asp Val Pro Pro Glu Gly Trp Asn Arg Thr Arg His Val Ile
                370                 375                 380

Ile Leu Met Thr Asp Gly Leu His Asn Met Gly Gly Asp Pro Ile Thr
385                 390                 395                 400

Val Ile Asp Glu Ile Arg Asp Leu Leu Tyr Ile Gly Lys Asp Arg Lys
                405                 410                 415

Asn Pro Arg Glu Asp Tyr Leu Asp Val Tyr Val Phe Gly Val Gly Pro
                420                 425                 430

Leu Val Asn Gln Val Asn Ile Asn Ala Leu Ala Ser Lys Lys Asp Asn
                435                 440                 445

Glu Gln His Val Phe Lys Val Lys Asp Met Glu Asn Leu Glu Asp Val
                450                 455                 460

Phe Tyr Gln Met Ile Asp Glu Ser Gln Ser Leu Ser Leu Cys Gly Met
465                 470                 475                 480

Val Trp Glu His Arg Lys Gly Thr Asp Tyr His Lys Gln Pro Trp Gln
                485                 490                 495

Ala Lys Ile Ser Val Ile Arg Pro Ser Lys Gly His Glu Ser Cys Met
                500                 505                 510

Gly Ala Val Val Ser Glu Tyr Phe Val Leu Thr Ala Ala His Cys Phe
                515                 520                 525

Thr Val Asp Asp Lys Glu His Ser Ile Lys Val Ser Val Gly Gly Glu
530                 535                 540

Lys Arg Asp Leu Glu Ile Glu Val Val Leu Phe His Pro Asn Tyr Asn
545                 550                 555                 560

Ile Asn Gly Lys Lys Glu Ala Gly Ile Pro Glu Phe Tyr Asp Tyr Asp
                565                 570                 575

Val Ala Leu Ile Lys Leu Lys Asn Lys Leu Lys Tyr Gly Gln Thr Ile
                580                 585                 590

Arg Pro Ile Cys Leu Pro Cys Thr Glu Gly Thr Thr Arg Ala Leu Arg
                595                 600                 605

Leu Pro Pro Thr Thr Thr Cys Gln Gln Gln Lys Glu Glu Leu Leu Pro
                610                 615                 620

Ala Gln Asp Ile Lys Ala Leu Phe Val Ser Glu Glu Lys Lys Leu
625                 630                 635                 640

Thr Arg Lys Glu Val Tyr Ile Lys Asn Gly Asp Lys Lys Gly Ser Cys
                645                 650                 655
```

-continued

```
Glu Arg Asp Ala Gln Tyr Ala Pro Gly Tyr Asp Lys Val Lys Asp Ile
            660             665             670

Ser Glu Val Val Thr Pro Arg Phe Leu Cys Thr Gly Gly Val Ser Pro
        675             680             685

Tyr Ala Asp Pro Asn Thr Cys Arg Gly Asp Ser Gly Gly Pro Leu Ile
    690             695             700

Val His Lys Arg Ser Arg Phe Ile Gln Val Gly Val Ile Ser Trp Gly
705             710             715             720

Val Val Asp Val Cys Lys Asn Gln Lys Arg Gln Lys Gln Val Pro Ala
                725             730             735

His Ala Arg Asp Phe His Ile Asn Leu Phe Gln Val Leu Pro Trp Leu
            740             745             750

Lys Glu Lys Leu Gln Asp Glu Asp Leu Gly Phe Leu
        755             760
```